US012558354B2

(12) United States Patent
Choi et al.

(10) Patent No.: US 12,558,354 B2
(45) Date of Patent: Feb. 24, 2026

(54) TUMOR NECROSIS FACTOR ALPHA (TNF-ALPHA) SMALL MOLECULE INHIBITOR

(71) Applicants: AJOU UNIVERSITY INDUSTRY-ACADEMIC COOPERATION FOUNDATION, Suwon-si (KR); UNIVERSITY-INDUSTRY COOPERATION GROUP OF KYUNG HEE UNIVERSITY, Yongin-si (KR)

(72) Inventors: Sang Dun Choi, Suwon-si (KR); Mahesh Chandra Patra, Suwon-si (KR); Nasir Javaid, Suwon-si (KR); Maria Batool, Suwon-si (KR); Dae-Hyun Hahm, Seoul (KR)

(73) Assignees: AJOU UNIVERSITY INDUSTRY-ACADEMIC COOPERATION FOUNDATION, Suwon-si (KR); UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 912 days.

(21) Appl. No.: 17/774,346

(22) PCT Filed: Nov. 5, 2020

(86) PCT No.: PCT/KR2020/015359

§ 371 (c)(1),
(2) Date: May 4, 2022

(87) PCT Pub. No.: WO2021/091238

PCT Pub. Date: May 14, 2021

(65) Prior Publication Data

US 2023/0000861 A1 Jan. 5, 2023

(30) Foreign Application Priority Data

Nov. 5, 2019 (KR) ........................ 10-2019-0140132

(51) Int. Cl.

| | |
|---|---|
| ***A61K 31/502*** | (2006.01) |
| ***A61P 29/00*** | (2006.01) |
| ***A61P 37/00*** | (2006.01) |
| ***C07D 417/12*** | (2006.01) |
| ***C07D 417/14*** | (2006.01) |

(52) U.S. Cl.

CPC ............ *A61K 31/502* (2013.01); *A61P 29/00* (2018.01); *A61P 37/00* (2018.01); *C07D 417/12* (2013.01); *C07D 417/14* (2013.01)

(58) Field of Classification Search

CPC ............................ C07D 417/12; A61K 31/502

See application file for complete search history.

(56) References Cited

U.S. PATENT DOCUMENTS 5,563,143 A 10/1996 Cohan et al.

FOREIGN PATENT DOCUMENTS

| | | | |
|---|---|---|---|
| KR | 10-2017-0092634 | A | 8/2017 |
| WO | 2007/119108 | A2 | 10/2007 |
| WO | 2010/108187 | A2 | 9/2010 |
| WO | 2010/151799 | A2 | 12/2010 |

OTHER PUBLICATIONS

Daniel Shiu-Hin Chan et al., "Structure-Based Discovery of Natural Product-Like TNF-α Inhibitors", Angew. Chem. Int. Ed. Engl., 2010, vol. 49, No. 16, pp. 2860-2864 (9 pages total).

Chien-Shu Chen et al., "Discovery of 3-(4-bromophenyl)-6-nitrobenzo[1.3.2]dithiazolium ylide 1,1-dioxide as a novel dual cyclooxygenase/5-lipoxygenase inhibitor that also inhibits tumor necrosis factor-α production", Bioorganic & Medicinal Chemistry, 2010, vol. 18, pp. 597-604 (8 pages total).

Si Chen et al., "Discovery of Novel Ligands for TNF-α and TNF Receptor-1 through Structure-Based Virtual Screening and Biological Assay", J. Chem. Inf. Model., 2017, vol. 57, No. 5, pp. 1101-1111 (23 pages total).

Hwanho Choi et al., "Discovery of the inhibitors of tumor necrosis factor alpha with structure-based virtual screening", Bioorganic & Medicinal Chemistry Letters, 2010, vol. 20, pp. 6195-6198 (4 pages total).

Emmanuel Coste et al., "Identification of small molecule inhibitors of RANKL and TNF signalling as anti-inflammatory and antiresorptive agents in mice", Ann. Rheum. Dis., 2013, pp. 1-7 (9 pages total).

Yekta Dowlati et al., "A Meta-Analysis of Cytokines in Major Depression", Biol. Psychiatry, 2010, vol. 67, pp. 446-457 (12 pages total).

Eran Elinav et al., "Inflammation-induced cancer: crosstalk between tumours, immune cells and microorganisms", Cancer, 2013, vol. 13, pp. 759-771 (13 pages total).

Michael J. Elliott et al., "Treatment of Rheumatoid Arthritis With Chimeric Monoclonal Antibodies to Tumor Necrosis Factor α", Arthritis & Rheumatism, 1993, vol. 36, No. 12, pp. 1681-1690 (10 pages total).

(Continued)

*Primary Examiner* — Golam M Shameem

(74) *Attorney, Agent, or Firm* — Sughrue Mion, PLLC

(57) ABSTRACT

A small molecule TNF-α inhibitor is disclosed. The compound has an activity of inhibiting the formation of a TNF-α homotrimer by specifically binding to the binding cavity of a TNF-α homodimer. A composition containing the compound as well as uses of the compound and the composition in preventing or treating autoimmune diseases and/or inflammatory diseases are disclosed. Extracellular inactivation of TNF-α through protein-protein interface destruction is the most innovative and effective method for alleviating chronic systemic inflammatory states, and TIM series compounds, which have better efficacy and lower toxicity than those of existing TNF inhibitors and have oral bioavailability, can be effectively used as leading anti-inflammatory molecules.

5 Claims, 10 Drawing Sheets

(56) References Cited

OTHER PUBLICATIONS

E. Esposito et al., "TNF-Alpha as a Therapeutic Target in Inflammatory Diseases, Ischemia-Reperfusion Injury and Trauma", Current Medicinal Chemistry, 2009, vol. 16, pp. 3152-3167 (16 pages total).
Lakshmi Ganesan et al., "The food colorant erythrosine is a promiscuous protein-protein interaction inhibitor", Biochemical Pharmacology, 2011, vol. 81, pp. 810-818 (9 pages total).
Sasker Grootjans et al., "Initiation and Execution mechanisms of necroptosis: an overview", Cell Death and Differentiation, 2017, vol. 24, pp. 1184-1195 (12 pages total).
Molly M. He et al., "Small-Molecule Inhibition of TNF-α", Science, 2005, vol. 310, pp. 1022-1025 (4 pages total).
Zhenlin Hu et al., "Japonicone A antagonizes the activity of TNF-α by directly targeting this cytokine and selectively disrupting its interaction with TNF receptor-1", Biochemical Pharmacology, 2012, vol. 84, pp. 1482-1491 (10 pages total).
William Humphrey et al., "VMD: Visual Molecular Dynamics", J. Mol. Graphics, 1996, vol. 14, pp. 33-38 (6 pages total).
Lingyan Jin et al., "Targeting Protein-Protein Interaction by Small Molecules", Annu. Rev. Pharmacol. Toxicol., 2014, vol. 54, pp. 435-456 (25 pages total).
Jeanne Keffer et al., " Transgenic mice expressing human tumour necrosis factor: a predictive genetic model of arthritis", The EMBO Journal, 1991, vol. 10, No. 13, pp. 4025-4031 (7 pages total).
Roland E. Kontermann et al., "Antagonists of TNF action: clinical experience and new developments", Expert Opin. Drug Discov., 2009, vol. 4, No. 3, pp. 279-292 (14 pages total).
Rashmi Kumari et al., "g_mmpbsa—A Gromacs Tool for High-Throughput MM-PBSA Calculations", Journal of Chemical Information and Modelling, 2014, vol. 54, pp. 1951-1962 (12 pages total).
Ping Li et al., "Drugs for Autoimmune Inflammatory Diseases: From Small Molecule Compounds to Anti-TNF Biologics", Frontiers in Pharmacology, 2017, vol. 8, Article 460, pp. 1-12 (12 pages total).
Krzysztof Lis et al., "Tumor necrosis factor inhibitors—state of knowledge", Arch. Med. Sci., 2014, vol. 6, pp. 1175-1185 (11 pages total).
Richard M. Locksley et al., "The TNF and TNF Receptor Superfamilies: Integrating Mammalian Biology", Cell, 2001, vol. 104, pp. 487-501 (15 pages total).
Li Ma et al., "A novel Small-molecule Tumor Necrosis Factor α Inhibitor Attenuates Inflammation in a Hepatitis Mouse Model", The Journal of Biological Chemistry, 2014, vol. 289, No. 18, p. 12457-12466 (10 pages total).
Georgia Melagraki et al., "Cheminformatics-aided discovery of small-molecule Protein-Protein Interaction (PPI) dual inhibitors of Tumor Necrosis Factor (TNF) and Receptor Activator of NF-κB Ligand (RANKL)", PLOS Computational Biology, 2017, pp. 1-27 (27 pages total).
Attila Mocsai et al, "What is the future of targeted therapy in rheumatology: biologics or small molecules?", BMC Medicine, 2014, vol. 12, No. 43, pp. 1-9 (9 pages total).
Claudia Monaco et al., "Anti-TNF Therapy: Past, Present and Future", International Immunology, 2014, pp. 1-36 (37 pages total).
Mahesh Chandra Patra et al., "Toll-like receptor-induced cytokines as immunotherapeutic targets in cancers and autoimmune diseases", Seminars in Cancer Biology, 2019 (Article in Process), 64:61-82 (accepted May 1, 2019), pp. 1-22 (22 pages total).
Victoria Richmond et al., "Small Molecules as Anti-TNF Drugs", Current Medicinal Chemistry, 2015, vol. 22, No. 25, pp. 2920-2942 (23 pages total).
Madhu Sudhana Saddala et al., "Identification of Novel inhibitors for TNFα, TNFR1 and TNFα-TNFR1 complex using pharmacophore-based approaches", Journal of Translational Medicine, 2019, vol. 17, No. 215, pp. 1-16 (17 pages total).
Thomas Sander et al., "DataWarrior: An Open-Source Program For Chemistry Aware Data Visualization and Analysis", Journal of Chemical Information and Modeling, 2014, pp. A-N (14 pages total).
Petros P. Sfikakis, "The First Decade of Biologic TNF Antagonists in Clinical Practice: Lessons Learned, Unresolved Issues and Future Directions", Curr. Dir. Autoimmun., 2010, vol. 11, pp. 180-210 (31 pages total).
Qi Shen et al., "Discovery of highly potent TNFα inhibitors using virtual screen", European Journal of Medicinal Chemistry, 2014, vol. 85, pp. 119-126 (8 pages total).
Antonia F. Stepan et al., "Structural Alert/Reactive Metabolite Concept as Applied in Medicinal Chemistry to Mitigate the Risk of Idiosyncratic Drug Toxicity: A Perspective Based on the Critical Examination of Trends in the Top 200 Drugs Marketed in the United States", Chemical Research in Toxicology, 2011, vol. 24, pp. 1345-1410 (66 pages total).
Martin Stroet et al., "The Automated Topology Builder Version 3.0 (ATB3.0): Prediction of Solvation Free Enthalpies in Water and Hexane", Journal of Chemical Theory and Computation, 2018, pp. 1-33 (34 pages total).
Hao Sun et al., "Metabolic Activation of a Novel 3-Substituted Indole-Containing TNF-α Inhibitor: Dehydrogenation and Inactivation of CYP3A4", Chem. Res. Toxicol., 2008, vol. 21, pp. 374-385 (12 pages total).
Walter Swardfager et al., "A Meta-Analysis of Cytokines in Alzheimer's Disease", Biol. Psychiatry, 2010, vol. 68, pp. 930-941 (12 pages total).
Adrian T. Ting et al., "More to life than NF-κB in TNFR1 Signaling", Trends in Immunology, 2016, pp. 1-11 (11 pages total).
H. Wajant et al., "Tumor necrosis factor signaling", Cell Death and Differentiation, 2003, vol. 10, pp. 45-65 (21 pages total).
Daniel Wendling et al., "Immunogenicity of TNF alpha inhibitors in rheumatology: many questions, enough answers?", Expert Opinion on Drug Safety, 2016, pp. 1-11 (12 pages total).
International Search Report dated Feb. 9, 2021 in International Application No. PCT/KR2020/015359.
Written Opinion of the International Searching Authority dated Feb. 9, 2021 in International Application No. PCT/KR2020/015359.
Mark James Abraham et al., "GROMACS: High performance molecular simulations through multi- level parallelism from laptops to supercomputers", SoftwareX, 2015, pp. 1-7 (7 pages total).
Bharat B. Aggarwal et al., "Historical perspectives on tumor necrosis factor and its superfamily: 25 years later, a golden journey", Blood, 2012, vol. 119, No. 3, pp. 651-665 (16 pages total).
Ali Akbar Alizadeh et al., "Identification of novel peptides against TNF-α using phage display technique and in silico modeling of their modes in binding", Pharmaceutical Sciences, 2016 (41 pages total).
Alessandro Annibaldi et al., "Checkpoints in TNF-Induced Cell Death: Implications in Inflammation and Cancer", Trends in Molecular Medicine, 2017, pp. 1-17 (17 pages total).
Michelle R. Arkin et al., "Small-molecule inhibitors of protein-protein interactions: progressing towards the reality", Chem Biol., 2014, vol. 21, No. 9, pp. 1102-1114 (31 pages total).
Jonathan B. Baell et al., "New Substructure Filters for Removal of Pan Assay Interference Compounds (PAINS) from Screening Libraries and for Their Exclusion in Bioassays", J. Med. Chem., 2010, vol. 53, No. 7, pp. 2719-2740 (22 pages total).
Priyanka Banerjee et al., "ProTox-II: a webserver for the prediction of toxicity of chemicals", Nucleic Acids Research, 2018, vol. 46, pp. W257-W263 (7 pages total).
Jun Soo Bang et al., "Anti-inflammatory and antiarthritic effects of piperine in human interleukin 1β- stimulated fibroblast-like synoviocytes and in rat arthritis models", Arthritis Research & Therapy, 2009, vol. 11, No. 2, pp. 1-9 (9 pages total).
B. Beutler et al., "Passive Immunization Against Cachectin/Tumor Necrosis Factor Protects Mice from Lethal Effect of Endotoxin", Science, 1985, vol. 229, pp. 869-871 (3 pages total).
Roy A. Black et al., "A metalloproteinase disintegrin that releases tumour-necrosis factor-α from cells", Nature, 1997, vol. 385, pp. 729-733 (5 pages total).

(56) References Cited

OTHER PUBLICATIONS

Jonathan M. Blevitt et al., "Structural Basis of Small-Molecule Aggregate Induced Inhibition of a Protein-Protein Interaction", Journal of Medicinal Chemistry, 2017, vol. 60, pp. 3511-3517 (7 pages total).
Dirk Brenner et al., "Regulation of tumour necrosis factor signalling: live or let die", Immunology, 2015, vol. 15, pp. 362-374 (13 pages total).
J Brynskov et al., "Tumour necrosis factor a converting enzyme (TACE) activity in the colonic mucosa of patients with inflammatory bowel disease", Gut, 2002, vol. 51, pp. 37-43 (7 pages total).
Yan Cao et al., "Identification of a ligand for tumor necrosis factor receptor from Chinese herbs by combination of surface plasmon resonance biosensor and UPLC-MS", Anal. Bioanal. Chem., 2016 (9 pages total).
Frank C. Victor et al., "TNF-alpha and apoptosis: implications for the pathogenesis and treatment of psoriasis", Journal of Drugs in Dermatology, 2002, vol. 1, No. 3, pp. 264-275 https://indexarticles.com/health-fitness/journal-of-drugs-in-dermatology/tnf-alphaand-apoptosis-implications-for-the-pathogenesis-and-treatment-of-psoriasis/ (17 pages total).
Database Registry CAS Registry No. 731828-65-2, Entered STN: Aug. 24, 2004, (1 Page).
Database Registry CAS Registry No. 849523-47-3 Entered STN: Apr. 29, 2005 (1 page).
Database Registry CAS Registry No. 852841-16-8 Entered STN: Jun. 23, 2005 (1 Page).
Database Registry CAS Registry No. 940245-87-4 Entered STN: Jun. 29, 2007 (1 Page).
Database Registry CAS Registry No. 1014217-64-1 Entered STN: Apr. 13, 2008 (1 Page).
Database Registry CAS Registry No. 1171311-99-1 Entered STN: Jul. 31, 2009 (1 Page).
Database Registry CAS Registry No. 1376321-02-6 Entered STN: Jun. 7, 2012 (1 Page).
Korean Office Action dated Sep. 6, 2024 in Application No. 10-2019-0140132.

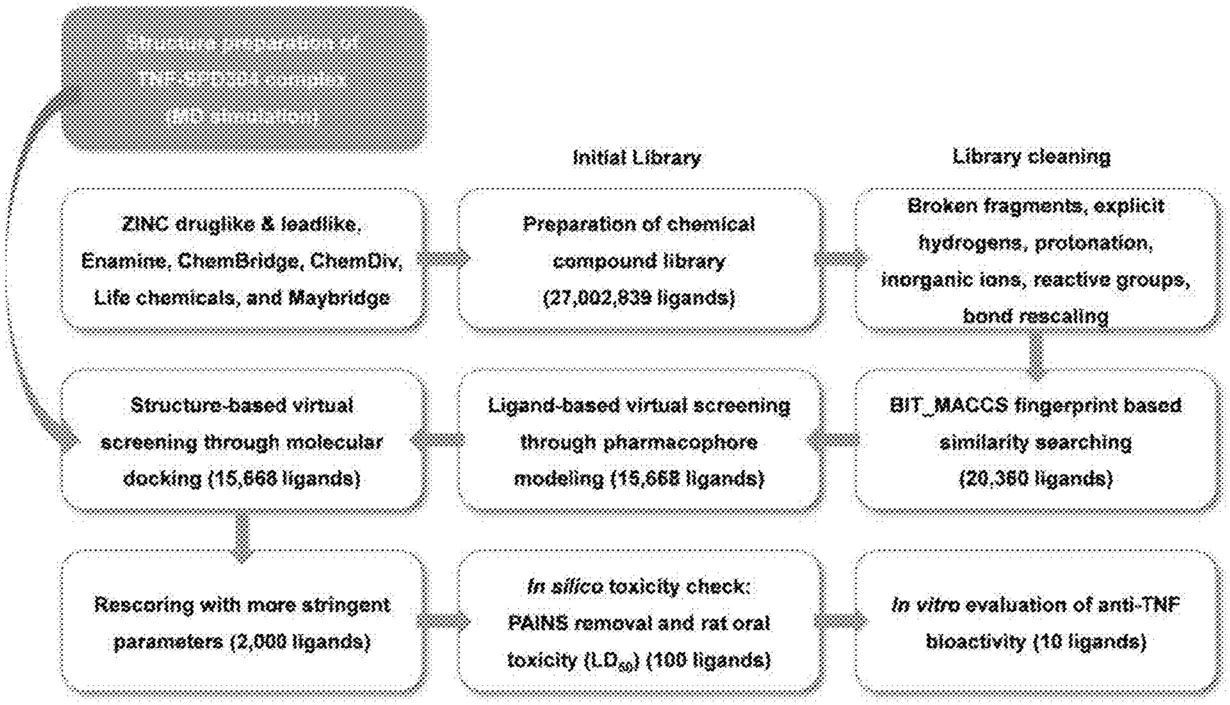
FIG. 1A
FIG. 1B
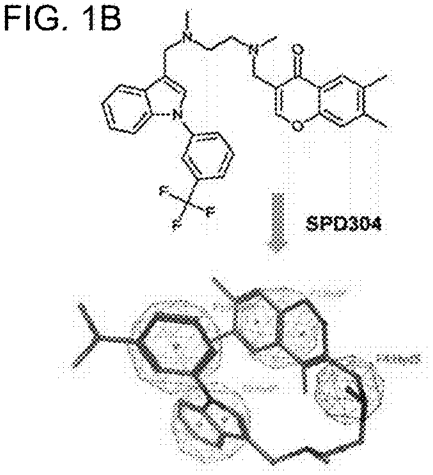
SPD304
FIG. 1C
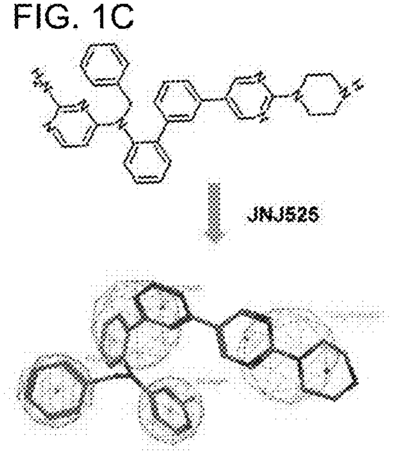
JNJ525
FIG. 1D
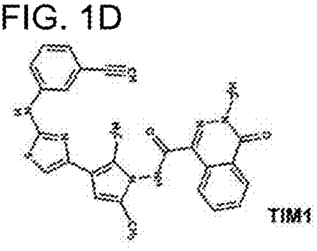
TIM1

Fig. 9

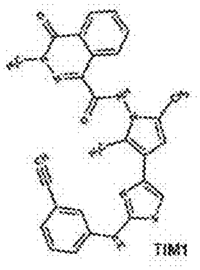

TIM1

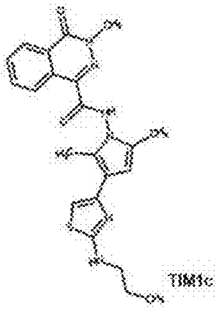

TIM1c

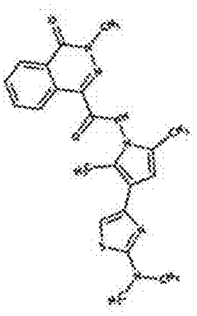

TIM1d

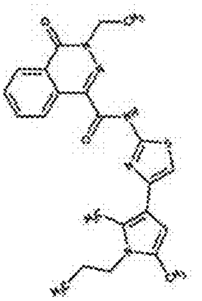

TIM1-7

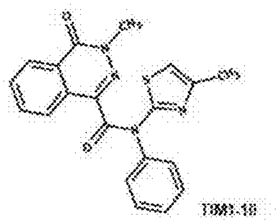

TIM1-10

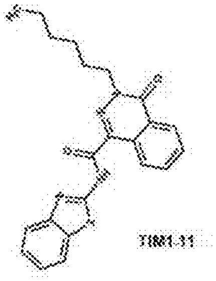

TIM1-11

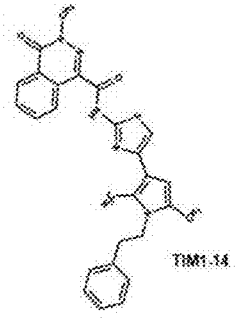

TIM1-14

| Name | SMILES | IUPAC Name | MW (g/mol) |
|---|---|---|---|
| TIM1 | Cc1cc(-c2csc(Nc3cccc(c3)C#C)n2)c(C)n1NC(=O)c1nn(C)c(=O)c2ccccc12 | N-[3-[2-[(3-ethynylphenyl)amino]-1,3-thiazol-4-yl]-2,5-dimethylpyrrol-1-yl]-3-methyl-4-oxophthalazine-1-carboxamide | 494.57 |
| TIM1c | Cl.CCCNc1nc(cs1)-c1cc(C)n(NC(=O)c2nn(C)c(=O)c3ccccc23)c1C | N-[2,5-dimethyl-3-[2-(propylamino)-1,3-thiazol-4-yl]pyrrol-1-yl]-3-methyl-4-oxophthalazine-1-carboxamide hydrochloride | 472.99 |
| TIM1d | CN(C)c1nc(cs1)-c1cc(C)n(NC(=O)c2nn(C)c(=O)c3ccccc23)c1C | N-[3-[2-(dimethylamino)-1,3-thiazol-4-yl]-2,5-dimethylpyrrol-1-yl]-3-methyl-4-oxophthalazine-1-carboxamide | 422.51 |
| TIM1-7 | CCCn1c(C)cc(-c2csc(NC(=O)c3nn(CC)c(=O)c4ccccc34)n2)c1C | N-[4-(2,5-dimethyl-1-propylpyrrol-3-yl)-1,3-thiazol-2-yl]-3-ethyl-4-oxophthalazine-1-carboxamide | 435.55 |
| TIM1-10 | Cc1csc(n1)N(C(=O)c1nn(C)c(=O)c2ccccc12)c1ccccc1 | 3-methyl-N-(4-methyl-1,3-thiazol-2-yl)-4-oxo-N-phenylphthalazine-1-carboxamide | 376.43 |
| TIM1-11 | CCCCCCn1nc(C(=O)Nc2nc3ccccc3s2)c2ccccc2c1=O | N-(1,3-benzothiazol-2-yl)-3-hexyl-4-oxophthalazine-1-carboxamide | 406.5 |
| TIM1-14 | Cc1cc(-c2csc(NC(=O)c3nn(C)c(=O)c4ccccc34)n2)c(C)n1CCc1ccccc1 | N-[4-[2,5-dimethyl-1-(2-phenylethyl)pyrrol-3-yl]-1,3-thiazol-2-yl]-3-methyl-4-oxophthalazine-1-carboxamide | 483.59 |

TUMOR NECROSIS FACTOR ALPHA (TNF-ALPHA) SMALL MOLECULE INHIBITOR

CROSS REFERENCE TO RELATED APPLICATIONS

This application is a National Stage of International Application No. PCT/KR2020/015359 filed on Nov. 5, 2020, claiming priority based on Korean Patent Application No. 10-2019-0140132 filed on Nov. 5, 2019.

TECHNICAL FIELD

The present invention relates to a small-molecule TNF-α inhibitor, and more particularly to a compound that inhibits the formation of a TNF-α homotrimer by specifically binding to the binding cavity of a TNF-α homodimer, a composition for inhibiting TNF-α comprising the same, and a composition for preventing or treating an autoimmune disease and/or an inflammatory disease comprising the composition for inhibiting TNF-α.

BACKGROUND ART

The tumor necrosis factor (TNF) superfamily constitutes a group of pleiotropic proinflammatory cytokines essential for several important physiological processes, such as host protection and tumor suppression (Aggarwal B. B. et al. (2012) Blood 119(3):651-665; Beutler B. et al. (1985) *Science* 229(4716):869-871). However, a dysregulated signaling of TNF subtypes (particularly TNF-α) is associated with several pathological conditions including rheumatoid arthritis, psoriasis (Victor F. C. & Gottlieb A. B. (2002) *J. Drugs Dermatol.* 1(3):264-275), and inflammatory bowel disease (Brynskov J. et al. (2002) Gut. 51(1):37-43). Chronic production of TNF-α is also associated with Alzheimer's disease (Swardfager W. et al. (2010) *Biol. Psychiatry* 68(10):930-941), major depression (Dowlati Y. et al. (2010) *Biol. Psychiatry* 67(5):446-457), and cancer (Locksley R. M. et al. (2001) *Cell* 104(4):487-501). Therefore, considerable efforts have been focused on disrupting the TNF signaling pathway using different types of therapeutic modulators (Monaco C. et al. (2015) *Int. Immunol.* 27(1):55-62).

TNF-α is initially synthesized as a 26 kDa 233-amino-acid transmembrane (TM) protein that after proteolytic cleavage (by TNF-α-converting enzyme) is released as a 17 kDa 157-amino-acid soluble protein. Soluble TNF-α (sTNF-α) is spontaneously assembled into stable homotrimers, which are biologically active forms of cytokines (Black R. A. et al. (1997) *Nature* 385(6618):729-733). TNF-α is mainly produced by macrophages, T lymphocytes, and natural killer cells, and is recognized by two distinct receptors, TNF receptor 1 (TNFR1) and TNFR2, leading to different signaling (Wajant H. et al. (2003) *Cell Death Differ.* 10(1):45-65). Although TNFR1 is ubiquitously expressed by all cell types, the expression of TNFR2 is limited to immune cells. Thus, the binding of TNF-α to each receptor has various functional consequences (Kontermann R. E. et al. (2009) *Expert Opin. Drug Discov.* 4(3):279-292). The downstream signaling pathway of TNFR1 typically activates transcription factors such as nuclear factor κ-light-chain-enhancer of activated B cells (NF-κB) and mitogen-activated protein kinases (MAPKs), including extracellular-signal-regulated kinase (ERK), p38 MAPK, and c-Jun N-terminal kinase (JNK) (Ting A. T. & Bertrand M. J. M. (2016) *Trends Immunol.* 37(8):535-545). Activation of NF-κB and MAPKs plays an important role in the induction of proinflammatory cytokines and immunoregulators, which exhibit strong inflammatory responses that often results in the apoptosis or necrosis of most cell types (Annibaldi A. & Meier P. (2018) *Trends Mol. Med.* 24(1):49-65).

It has been suggested that dysregulation of TNF production is associated with chronic arthritis in a mouse model and that the application of TNF inhibitors is effective against the disease (Keffer J. et al. (1991) *EMBO J.* 10(13):4025-4031). This observation had aroused great interest among anti-TNF manufacturers, leading to the first successful clinical trials for chronic inflammatory diseases including rheumatoid arthritis (Elliott M. J. et al. (1993) *Arthritis Rheum.* 36(12):1681-1690), Crohn's disease, psoriasis, psoriatic arthritis, juvenile idiopathic arthritis, spondyloarthritis, and Behcet's disease (Sfikakis P. P. (2010) *Curr. Dir. Autoimmun.* 11:180-210). Currently approved drugs for the treatment of inflammatory diseases are synthetic monoclonal antibodies such as infliximab, adalimumab, certolizumab, and golimumab, or receptor fusion proteins such as etanercept, and all of these drugs bind to sTNF-α to thus prevent its association with TNFR1 or TNFR2 (Lis K. et al. (2014) *Arch. Med. Sci.* 10(6):1175-1185). Although clinically successful, these biologics are expensive, not available for oral administration, and sometimes undermine the host immunity to latent or recurring infections (Wendling D. et al. (2017) *Expert Opin. Drug Saf.* 16(1):1-3). Therefore, small-molecule-based therapy is perceived as a potential alternative to TNF-α inhibition using biologics (Richmond V. et al. (2015) *Curr. Med. Chem.* 22(25):2920-2942). SPD304, which is the first antagonist of TNF-α, was developed through structure-based drug design (He M. M. et al. (2005) *Science* 310 (5750):1022-1025). Subsequent studies revealed the structure of TNF-α bound to multiple copies of ligand JNJ525, indicating possible aggregation-mediated TNF inhibition (Blevitt J. M. et al. (2017) *J. Med. Chem.* 60(8):3511-3517). A recent study proposed small molecules that directly bind to TNF-α with $IC_{50}$ in the range of 1-50 μM and block TNFR1- or TNFR2-mediated downstream signaling pathways (Chen C. S. et al. (2010) *Bioorg. Med. Chem.* 18 (2):597-604). Compounds resembling natural products, which regulate TNF-α-mediated cellular effects, have also been found in both in vitro and in vivo studies (Hu Z. et al. (2012) *Biochem. Pharmacol.* 84(11):1482-1491). Despite preclinical advances in anti-TNF biology, the low potency and high toxicity of these chemicals have limited testing in clinical trials lately.

Accordingly, the present inventors have made great efforts to develop small-molecule TNF-α inhibitors, identified a series of novel small-molecule TNF-α inhibitors designated as TNF inhibitory molecules (TIM) through a combined structure-based and ligand-based virtual screening approach, and ascertained that through in vitro bioassay, the lead material TIM1 significantly inhibits TNF-α-mediated secretion of cytokines, does not show cytotoxicity up to 200 μM, and attenuates TNF-α-induced cell death in both mouse and human cell types. Moreover, it has been confirmed that TIM1 is capable of stably occupying the central hydrophobic cavity in a TNF-α homodimer through cross-linking experiments, Western blotting, and computational modeling, and also that it is possible to prevent binding of the third monomer, which is necessary for the formation of a functional homotrimer. Furthermore, it has been confirmed that among the derivatives of TIM1, TIM1c exhibits oral bioactivity in a mouse model of collagen-induced polyarthritis and suppresses arthritis symptoms to a level resembling healthy mice. Consequently, it has been confirmed that the TIM series is capable of playing a role as a potent lead compound for the development of small-molecule compound therapeutic agents that alleviate TNF-mediated autoimmune diseases and/or inflammatory diseases, thus culminating in the present invention.

The information described in the Background Art is only for improving understanding of the background of the present invention, and it is not to be construed as including information forming the related art, which is already known to those of ordinary skill in the art to which the present invention belongs.

SUMMARY OF THE INVENTION

It is an object of the present invention to provide a small-molecule compound having effects of inhibiting TNF-α-mediated cytokine secretion and attenuating TNF-α-induced cell death, and a composition for inhibiting TNF-α comprising the same.

It is another object of the present invention to provide a composition for preventing or treating an autoimmune disease and/or an inflammatory disease comprising the composition for inhibiting TNF-α.

It is still another object of the present invention to provide a method of preventing or treating an autoimmune disease and/or an inflammatory disease comprising administering the composition for inhibiting TNF-α.

It is yet another object of the present invention to provide the use of the composition for inhibiting TNF-α for the prevention or treatment of an autoimmune disease and/or an inflammatory disease.

It is still yet another object of the present invention to provide the use of the composition for inhibiting TNF-α for the manufacture of a medicament for the prevention or treatment of an autoimmune disease and/or an inflammatory disease.

In order to accomplish the above objects, the present invention provides a compound represented by Chemical Formula 1 below or a pharmaceutically acceptable salt thereof.

[Chemical Formula 1]

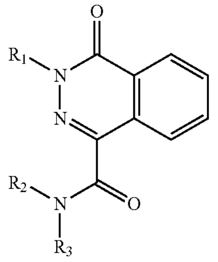

In Chemical Formula 1, $R_1$ to $R_3$ are each independently a hydrogen atom, straight or branched alkyl, amino, alkylamino, arylamino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, in which the alkyl, alkylamino or alkoxy is $C_{1-30}$, the cycloalkyl is $C_{3-30}$, the allyl is $C_{2-30}$, the aryl is $C_{6-30}$, and the heteroaryl and heterocycloalkyl contain a heteroatom selected from among oxygen (O), sulfur (S), and nitrogen (N).

In addition, the present invention provides a composition for inhibiting TNF-α comprising the compound or the pharmaceutically acceptable salt thereof.

In addition, the present invention provides a composition for preventing or treating an autoimmune disease and/or an inflammatory disease comprising the composition for inhibiting TNF-α.

In addition, the present invention provides a method of preventing or treating an autoimmune disease and/or an inflammatory disease comprising administering the composition for inhibiting TNF-α.

In addition, the present invention provides the use of the composition for inhibiting TNF-α for the prevention or treatment of an autoimmune disease and/or an inflammatory disease.

In addition, the present invention provides the use of the composition for inhibiting TNF-α for the manufacture of a medicament for the prevention or treatment of an autoimmune disease and/or an inflammatory disease.

BRIEF DESCRIPTION OF DRAWINGS

FIGS. 1A to 1D show the overall virtual screening workflow according to the present invention.

FIG. 1A schematically shows various stages of chemical library preparation and virtual screening, with the number of output ligands in each stage indicated in parentheses. FIG. 1B shows the two-dimensional structures of the active compound TIM1 and two TNF inhibitors SPD304 (PDB ID: 2AZ5) and JNJ525 (PDB ID: 5MU8). FIG. 1C shows the pharmacophore models of SPD304 and JNJ525 utilized for ligand-based virtual screening. FIG. 1D shows the two-dimensional structure of TIM1.

FIG. 2A shows cell viability analysis (MTT assay) of 10 in silico-derived hit molecules in human dermal fibroblasts (HDFs), in which cells ($10^4$/well) were incubated with each ligand at three concentrations (1, 10 and 50 μM) for 24 hours, and TNF inhibitors C87 and SPD304 were used as positive controls. FIG. 2B shows the inhibition of human interleukin 8 (hIL-8) secretion by TIM1 and SPD304, FIG. 2C shows the inhibition of human interleukin 6 (hIL-6) secretion by TIM1 and SPD304, in which TIM1 and SPD304 at four concentrations (1, 10, 50 and 100 μM) pre-incubated with recombinant human tumor necrosis factor α (1 ng/ml) for 1 hour were applied to HDFs for 24 hours, and the levels of hIL-8 and hIL-6 were represented as data after analysis using respective enzyme-linked immunosorbent assay (ELISA) kits and normalization with respect to controls. FIG. 2D shows the $IC_{50}$ curve of TIM1 against the secretion of hIL-8 in HDFs, FIG. 2E shows the $IC_{50}$ curve of TIM1 against the secretion of hIL-6 in HDFs, in which the $IC_{50}$ values were measured using data obtained through ELISA experiments. FIG. 2F shows the analysis of cell viability through an MTT assay after treatment with TIM1 and SPD304, in which the ELISA experiments were independently performed 4 times, and mean±SEM of the experiments was evaluated using a two-tailed paired Student's t test (*$P<0.05$).

FIG. 3A shows the comparative death rate (%) induced by TIM1 or SPD304 at different concentrations (1, 10, 50 and 100 μM) pre-incubated with recombinant human tumor necrosis factor α [rhTNF-α; (10 ng/ml)] in human dermal fibroblasts (HDFs; $10^4$/well), FIG. 3B shows the death attenuation rate (%) by TIM1 or SPD304 pre-incubated with recombinant mouse tumor necrosis factor α (rmTNF-α) and murine fibrosarcoma L929 cells, in which cell viability was measured using an MTT assay, 24 hours after treatment. FIG. 3C shows the HDF cell morphology after treatment with TIM1 or SPD304, FIG. 3D shows the L929 cell morphology after treatment with TIM1 or SPD304, in which the images of the treated cells were captured by means of an inverted microscope at 10× magnification, and surviving cells represented by white arrows. FIG. 3E shows the $IC_{50}$ determination curve representing the cell death attenuation potential of TIM1 pre-incubated with rhTNF-α in HDFs, FIG. 3F shows the $IC_{50}$ determination curve representing the cell death attenuation potential of TIM1 pre-incubated with rmTNF-α in L929 cells, in which $IC_{50}$ values were calculated from the data obtained through an MTT assay, curve fitting and calculation were performed using GraphPad Prism 7 (GraphPad Software, San Diego, CA) by nonlinear regression analysis, and all experiments were independently performed 4 times, mean±SEM of the independent experiments being calculated using a two-tailed paired Student's t-test (*P<0.05).

FIG. 4A shows extracellular-signal-regulated kinase (p-ERK), p38-MAPK (p-p38), and c-Jun N-terminal kinase (p-JNK) after TIM1 treatment, which are the results of Western blotting representing reduced phosphorylation of the p65 (p-p65) subunit of nuclear factor kappa-light-chain-enhancer of activated B cells (NF-κB) and mitogen-activated protein kinases (MAPKs), in which L929 cells were seeded on a 6 cm dish and treated with recombinant mouse TNF-α (rmTNF-α; 1 ng/ml) alone or a pre-incubated mixture of TIM1 (20 μM) and rmTNF-α (1 ng/ml) for 5, 10, 15 or 30 minutes, and total protein extraction and Western blotting of signaling components were performed using primary and secondary antibodies against the respective proteins. FIG. 4B shows the results of Western blotting representing the reduction of cleaved caspase 3 (c-Cas3) and caspase 8 (c-Cas8) by TIM1, in which Western blotting was visualized with a CHEMIDOC™ Touch Imaging System (Bio-Rad Laboratories) and β-actin protein was used as an endogenous control.

FIG. 6A shows the human interleukin-8 (hIL-8) inhibition profile of TIM1 derivatives, in which a 1-hr pre-incubated mixture of recombinant human TNF-α (1 ng/ml) with the compound at various concentrations (1, 10, and 50 μM) was applied to human dermal fibroblasts, followed by culture for 24 hours, after which the level of hIL-8 was analyzed using a relevant ELISA kit and data thereof were represented after normalization with respect to a control, all ELISA experiments being independently performed 5 times, each experiment being in duplicate, mean±SEM of the independent experiments being calculated using a two-tailed paired Student's t-test (*P<0.05). FIG. 6B is a graph showing body weight, FIG. 6C is a graph showing a squeaking number (the value 0 indicating no sign of pain), FIG. 6D is a graph showing an increase in paw volume, FIG. 6E is a graph showing an arthritis index, that is, the severity of mouse limb arthritis. The number of arthritic limbs was quantified, and each limb was assigned a severity score of 0-4, the data representing the number of arthritic limbs per arthritic mouse and the mean severity score of arthritis in each limb, black arrows representing the start date of drug administration, NOR, n=4; CIA, n=4; TIM1c_2 mg/ml, n=4; TIM1c_20 mg/ml, n=5, values being represented as means±SEM. #p<0.05, ##p<0.01, ###p<0.001 vs. NOR group and p<0.05, p<0.01, *p<0.001 vs. CIA group (two-way ANOVA followed by Bonferroni correction). FIG. 6F shows the swelling of each group of the forelimbs and hindlimbs of arthritic mice.

FIG. 7A shows the interaction between SPD304 and the central hydrophobic cavity of TNF-α, FIG. 7B shows the interaction between TIM1 and the ligand-binding cavity of TNF-α, and FIG. 7C shows the interaction between TIM1c and the ligand-binding cavity of TNF-α, in which magnified views are shown on the right for detailed visualization of intermolecular interactions. Chain A and chain B of TNF-α are shown in blue and green, respectively, the bound ligands are represented as a stick model in the center of the cavity with the carbon atoms represented in white, the key residues Y119/Y119* in two subunits is represented as orange stick, and '*' in the residue number represents chain B of TNF-α.

FIG. 8A is a graph showing the effects of TIM1 and a solvent thereof, DMSO, on the viability of human dermal fibroblasts, in which cells ($10^4$/well) were treated with DMSO at 3 different concentrations (0.5, 1, and 2%) and TIM1 at 8 different concentrations (1, 3.125, 6.25, 12.5, 25, 50, 100, and 200 μM) for 24 hours, and the cell viability was monitored by an MTT assay. FIG. 8B is a graph showing the effect of TIM1 on the viability of a mouse fibrosarcoma cell line [L929 ($1.5\times10^4$/well)] under the same conditions as in FIG. 8A. All experiments were independently performed 4 times, and mean±SEM of the independent experiments was calculated using a two-tailed paired Student's t-test (*P<0.05).

FIG. 9 shows SMILES strings, IUPAC names and molecular weights of all active ligands.

DETAILED DESCRIPTION AND PREFERRED EMBODIMENTS OF THE INVENTION

Figures 2A, 2B, 2C, 2D, 2E, 2F:
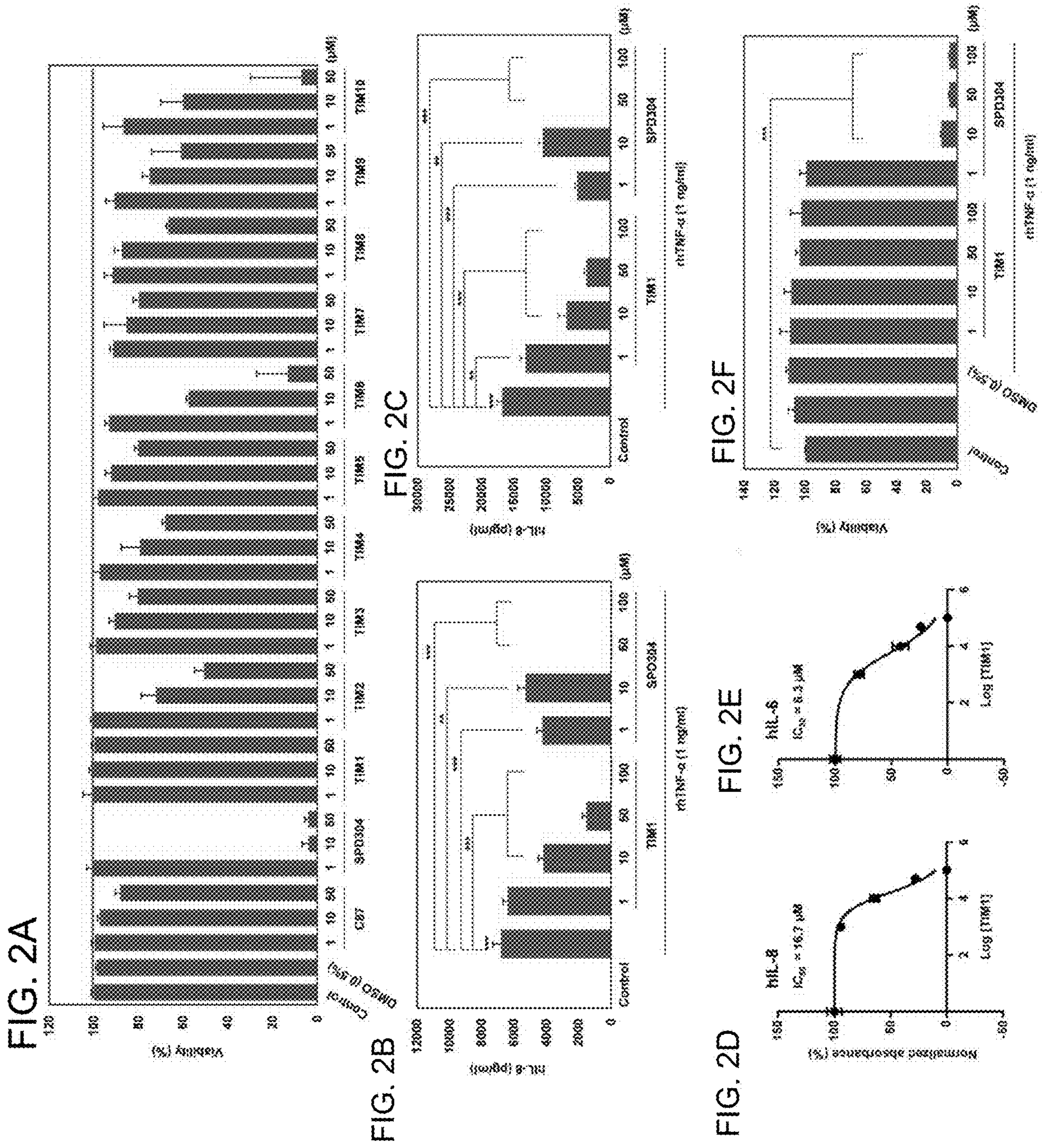
FIGS. 2A to 2F show the screening and identification of potential tumor necrosis factor α (TNF-α) inhibitors.

Unless otherwise defined, all technical and scientific terms used herein have the same meanings as those typically understood by those skilled in the art to which the present invention belongs. In general, the nomenclature used herein is well known in the art and is typical.

Tumor necrosis factor alpha (TNF-α) is induced by the TNF receptor 1-mediated death signaling pathway, and strongly induces necrosis, which is a form of cell death. Compounds that directly inhibit TNF-α have long been considered as alternative therapies to biological products, such as antibodies, which are currently approved for the treatment of systemic inflammatory diseases such as rheumatoid arthritis, psoriatic arthritis, and Crohn's disease. Due to the severity of diseases associated with the dysregulated TNF-α-TNFR1 signaling axis, there is increasing need to develop potent molecules capable of preventing TNF-α-mediated inflammatory and necrotic pathways (Li P., Zheng Y. & Chen X. (2017) *Front Pharmacol.* 8:460).

The X-ray crystallographic structure of TNF-α complexed with the TNF-α inhibitor SPD304 makes it possible to screen many multiconformational libraries using the principle of computational drug discovery. The present inventors have identified a novel lead compound, TIM1, which is not toxic to cells and inhibits TNF-α-induced toxicity in both human and mouse cell lines. Through comparison with the known inhibitor SPD304, it has been confirmed that TIM1 had relatively low toxicity for TNF-α signaling and had significant inhibitory activity. In addition, the compound TIM1c was demonstrated to be the most active TNF inhibitor among all TIM1 derivatives, exhibited oral bioavailability in a CIA mouse model, and suppressed various arthritis symptoms in mice.

The inhibitor, defined as TNF inhibitory molecule 1 (TIM1), had an $IC_{50}$ (half-maximal inhibitory concentration) of 26.2 μM (in a human cell line) and 24.9 μM (in a mouse cell line), exhibited negligible cytotoxicity compared to the known inhibitor SPD304, and showed an excellent attenuation effect in TNF-α-induced cell death. In addition, the compound exhibited inhibitory effects by blocking, in L929 cells, NF-κB (nuclear factor κ-light-chain-enhancer of activated B cells), MAPKs (mitogen-activated protein kinases), and caspase 3- and 8-dependent proapoptotic pathways. The $IC_{50}$ values of TIM1 for secretion of TNF-α-mediated interleukin 6 and interleukin 8 in human dermal fibroblasts (HDFs) were calculated to be 6.3 μM and 16.71 μM, respectively. In the present invention, it was demonstrated that the compound inactivates the function of TNF-α by disrupting the homotrimerization assembly and prevents binding to the TNF receptor. One of the TIM1 derivatives, TIM1c, showed the most potent in vitro activity and oral bioavailability in a mouse model of collagen-induced polyarthritis, and this compound inhibited paw swelling, weight loss, and the number of squeaks, and decreased all arthritis indexes in mice. Therefore, TIM series compounds are capable of acting as potent lead materials in the development of alternatives to anti-TNF biological products.

The computational modeling suggests that TIM1/TIM1c has good shape complementarity to the central hydrophobic cavity of the TNF-α dimer, having a thiazole ring stacked between the Y119 residues of both monomers. It has been revealed that Y119 is essential for coordinating monomer assembly and receiving inhibitors in the binding cavity of TNF-α (He M. M. et al. (2005) *Science* 310(5750):1022-1025). Most TNF-α-TIM1 or TNF-α-TIM1c complexes are stabilized through intermolecular hydrogen bonding or hydrophobic contact without salt bridges. Since the ligand-binding cavity on the TNF-α dimer has a predominantly flat surface due to an aromatic ring structure such as tyrosine, the ligand must be hydrophobic and large enough to occupy the cavity in an expanded form (Jin L., Wang W. & Fang G. (2014) *Annu. Rev. Pharmacol. Toxicol.* 54:435-456). Chemical cross-linking and Western blotting analysis clearly showed that TIM1 is a specific and potent disruptor of TNF-α homotrimerization. Based on these results, proposed are two possible scenarios for the mechanism of action of TIM1 or potent derivatives thereof (e.g. TIM1c). First, the ligand promotes the formation of a stable homodimer by mimicking the third monomer during assembly. Second, the ligand binds to the homodimer only after the third monomer spontaneously dissociates and prevents subsequent reassembly of the functional trimer. A third mechanism of action may be as follows: the ligand interacts with the preformed homotrimer to displace one of the monomers from the trimeric assembly. Since the ligand-binding moiety of the TNF-α monomer is buried at the protein-protein interface, the inhibitor has to overcome a significant energy barrier in order to dissociate the preformed trimer (Arkin M. R., Tang Y. & Wells J. A. (2014) *Chem. Biol.* 21(9):1102-1114).

For a few known TNF-α inhibitors, the definite mechanism of their inhibitory action has been determined. Ligands are capable of blocking the cellular effect of TNF-α, for example, (i) by interacting with the receptor-binding surface of TNF-α (Ma L. et al. (2014) *J. Biol. Chem.* 289(18):12457-12466), (ii) by interacting with the TNF-binding surface of the receptor (Chen S. et al. (2017) *J. Chem. Inf. Model* 57(5):1101-1111), (iii) by disrupting the trimerization interface of TNF-α (Chan D. S. et al. (2010) *Angew Chem. Int. Ed. Engl.* 49(16):2860-2864), or (iv) by blocking TNF-α-converting enzymes or other downstream signaling molecules (Esposito E. & Cuzzocrea S. (2009) *Curr. Med. Chem.* 16(24):3152-3167). Although all of these approaches have been relatively effective at downregulating TNF-mediated signaling pathways, extracellular inactivation of TNF-α due to disruption of the protein-protein interface is regarded as the most innovative and effective method for alleviating a chronic systemic inflammatory status. This approach is similar to approaches using antibodies or receptor fusion proteins that irreversibly bind to TNF-α and neutralize interactions with the receptor with maximal specificity.

Figure 8A:
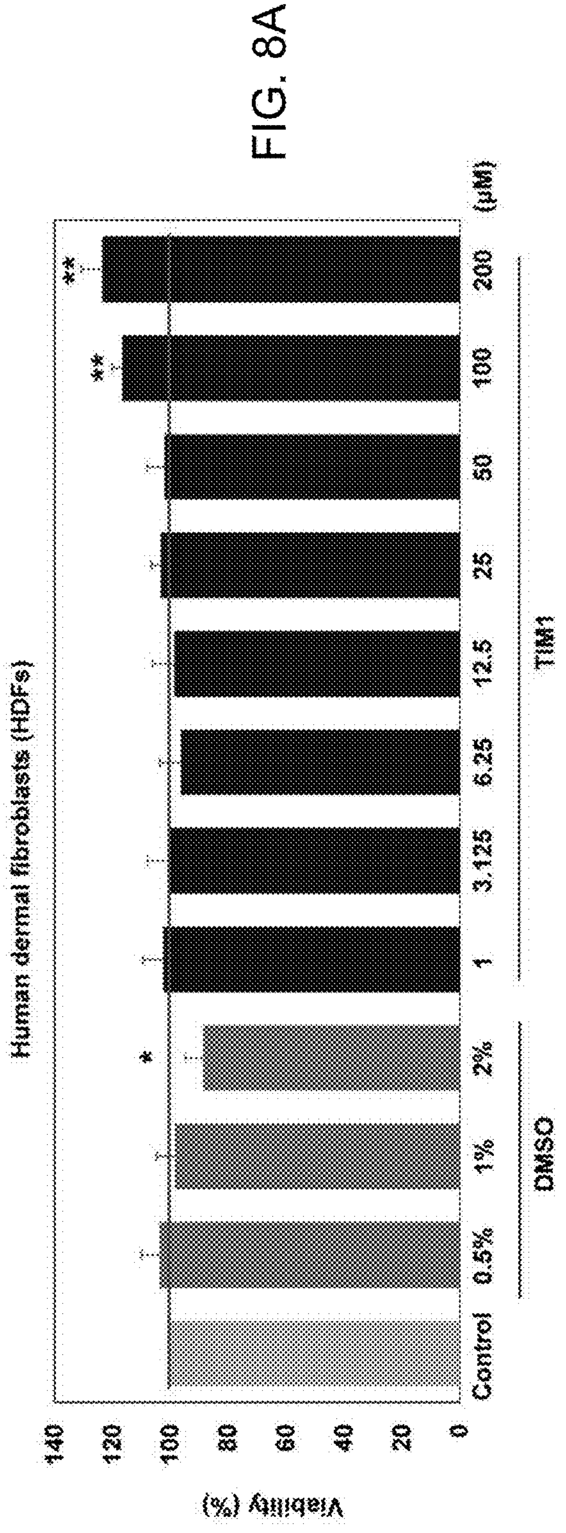
FIGS. 8A and 8B are a graph showing the cytotoxicity analysis of the novel ligand TIM1 at increasing concentrations.
Figure 8B:
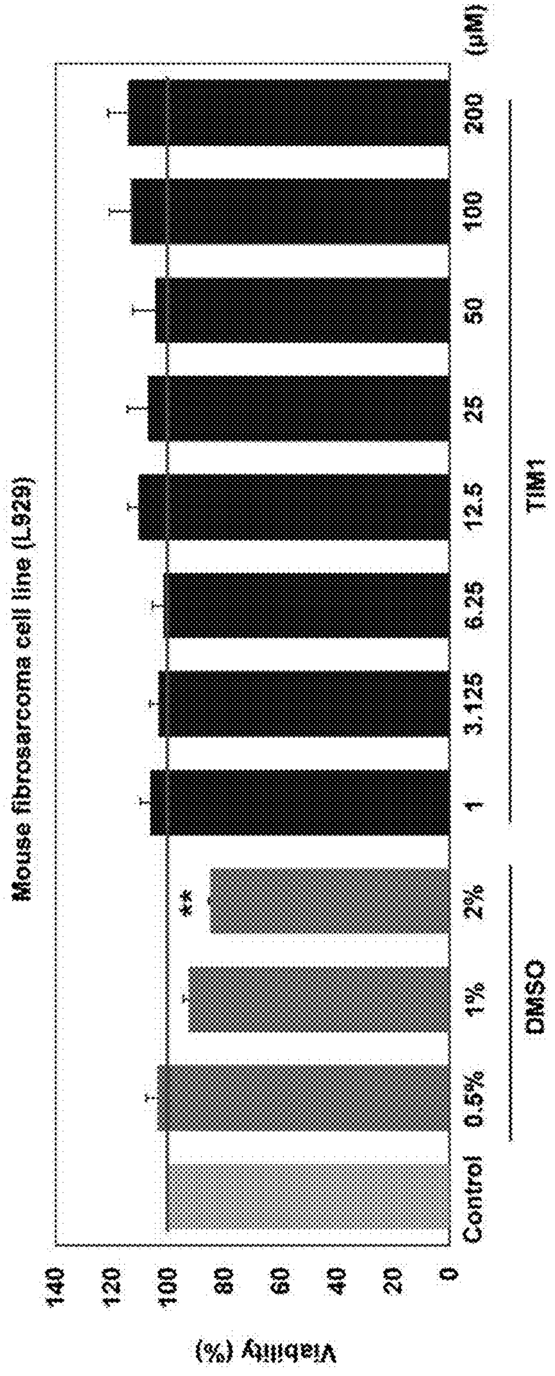

The present inventors evaluated the two TNF inhibitors, SPD304 and C87, as positive controls, and simultaneously confirmed and compared the inhibitory activity of TIM1 in a cell viability assay. Unlike SPD304, C87 has been reported to inhibit TNF-α signaling by an unknown mechanism that does not involve disruption of the homotrimerization interface (Ma L. et al. (2014) *J. Biol. Chem.* 289(18):12457-12466). Therefore, C87 was excluded from further activity comparison with TIM1 because these two have different mechanisms of action. TIM1 had high efficacy in inhibiting TNF-α-induced cytokine secretion and death of inflammatory cells, and did not exhibit cytotoxicity even at high concentrations (up to 100 μM). The toxicity of a given ligand is usually due to intrinsic chemical scaffolds that may interfere with various host pathways after metabolic degradation (Stepan A. F. et al. (2011) *Chem. Res. Toxicol.* 24(9):1345-1410). A similarity search in chemical database (e.g. PubChem) confirmed that TIM1/TIM1c did not contain any fragments previously known to interact with essential host molecules, indicating good absorption, distribution, metabolism, and excretion (ADME) characteristics. In this regard, SPD304 was observed to have an inconsistent effect on cytokine secretion at different concentrations. For example, inhibition of cytokine secretion was weak at 10 μM but stronger at 1 μM, while significant cytotoxic effects were exhibited at concentrations of 10, 50 or 100 μM. This inconsistent activity of SPD304 may be due to certain chemical properties that may interfere with important physiological processes in cells. The 3-alkylindole moiety of the ligand is metabolized by cytochrome P450 to thus generate reactive electrophilic iminium ions that are able to react with major intracellular proteins and DNA (Sun H. & Yost G. S. (2008) *Chem. Res. Toxicol.* 21(2):374-385). Moreover, C87 showed mild toxicity to HDFs. In contrast, TIM1 did not show any signs of cytotoxicity at the concentrations tested. At low concentrations (i.e. ~1 μM), TIM1 is somewhat less effective than SPD304, but the safety profile thereof is vastly superior from a therapeutic standpoint (FIGS. 8A and 8B).

The present inventors have ascertained that TIM1c, one of the TIM1 derivatives, has oral activity and is capable of suppressing systemic inflammation in a CIA mouse model. Currently, only anti-TNF antibodies or decoy receptors are approved for therapeutic administration for the treatment of diseases such as RA, psoriatic arthritis, and ankylosing spondylitis (Patra M. C., Shah M. & Choi S. (2019) *Semin. Cancer Biol*). Previously, several peptide/peptidomimetic-based TNF-α inhibitors have been identified through phage display or inferential design approaches (Sun H. & Yost G. S. (2008) *Chem. Res. Toxicol.* 21(2):374-385; Alizadeh A. A. et al. (2017) *Eur. J. Pharm. Sci.* 96:490-498). Nevertheless, small-molecule products are preferred over peptides or proteins because of the desirable pharmacokinetic endpoints thereof, and provide drugs having improved bioavailability and metabolic stability (Mocsai A., Kovacs L. & Gergely P. (2014) *BMC Med.* 12:43). A small number of TNF-blocking small molecules have been demonstrated to be effective via oral routes in animals (Cost E. et al. (2015) *Ann. Rheum. Dis.* 74(1):220-226). The efficacy of TIM1c on CIA mice suggests that TIM series compounds may make a useful contribution to existing research on the treatment or prevention of TNF-mediated inflammatory diseases through the use of low-molecular-weight drugs.

In summary, it is possible to obtain novel small-molecule ligands having the ability to inhibit TNF-α function by interfering with homotrimerization assembly through the virtual screening workflow according to the present invention. Compared to existing TNF inhibitors, TIM series compounds having oral efficacy in mice and a low toxicity profile may be developed and characterized in the future as valuable anti-inflammatory lead molecules.

Accordingly, in one aspect, the present invention is directed to a compound represented by Chemical Formula 1 below or a pharmaceutically acceptable salt thereof.

[Chemical Formula 1]

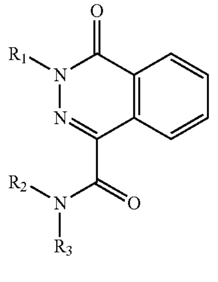

In Chemical Formula 1, $R_1$ to $R_3$ are each independently a hydrogen atom, straight or branched alkyl, amino, alkylamino, arylamino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, in which the alkyl, alkylamino, or alkoxy is $C_{1-30}$, the cycloalkyl is $C_{3-30}$, the allyl is $C_{2-30}$, the aryl is $C_{6-30}$, and the heteroaryl and heterocycloalkyl contain a heteroatom selected from among oxygen (O), sulfur (S), and nitrogen (N).

In the present invention, the alkyl, alkylamino or alkoxy is preferably $C_{1-20}$, more preferably $C_{1-12}$, and most preferably $C_{1-6}$.

As used herein, the term "$C_{1-30}$ alkyl" refers to a monovalent linear or branched saturated hydrocarbon moiety having 1 to 30 carbon atoms and consisting only of carbon and hydrogen atoms. Examples of the alkyl group include, but are not limited to, methyl, ethyl, propyl, isopropyl, butyl, isobutyl, sec-butyl, tert-butyl, and the like. Examples of "branched alkyl" include isopropyl, isobutyl, tert-butyl, and the like.

The term "$C_{1-30}$ alkoxy" refers to a chemical formula —O—$C_{1-30}$ alkyl, and includes, for example, methoxy, ethoxy, isopropoxy, tert-butoxy, and the like, but is not limited thereto.

Specific examples of the term "halogen (or halo)" include fluorine (F), chlorine (Cl), bromine (Br), and iodine (I).

The term "$C_{6-30}$ aryl" includes at least one ring having a shared pi electron system, for example a monocyclic or fused-ring polycyclic group (i.e. rings that share adjacent pairs of carbon atoms). Unless otherwise defined herein, the aryl may include phenyl, naphthyl, and biaryl. In an embodiment of the present invention, the aryl is an aromatic ring having 6 to 30 carbon atoms.

The term "$C_{3-30}$ cyclic alkyl" refers to a cyclic saturated hydrocarbon moiety having 5 to 6 carbon atoms and consisting only of carbon and hydrogen atoms. Examples of such a cyclic alkyl group include, but are not limited to, cyclopentyl, cyclohexyl, and the like.

Unless otherwise defined, the term "heteroaryl" refers to a 5- or 6-membered aromatic ring containing 1 to 4 heteroatoms selected from the group consisting of N, O, and S, or a bicyclic ring in which the heteroaryl ring is fused to a benzene ring or another heteroaryl ring. Examples of monocyclic heteroaryl include thiazolyl, oxazolyl, thiophenyl, furanyl, pyrrolyl, imidazolyl, isoxazolyl, isothiazolyl, pyrazolyl, triazolyl, triazinyl, thiadiazolyl, tetrazolyl, oxadiazolyl, pyridinyl, pyridazinyl, pyrimidinyl, pyrazinyl, and groups similar thereto, but are not limited thereto. Examples of bicyclic heteroaryl include indolyl, azaindolyl, indolinyl, benzothiophenyl, benzofuranyl, benzimidazolyl, benzoxazolyl, benzisoxazolyl, benzothiazolyl, benzothiadiazolyl, benzotriazolyl, quinolinyl, isoquinolinyl, purinyl, furopyridinyl, and groups similar thereto, but are not limited thereto.

The term "heterocycloalkyl" refers to a saturated or partially unsaturated 5- to 9-membered carbocyclic ring containing 1 to 3 heteroatoms selected from among N, O, and S, in addition to carbon atoms. For example, heterocyclyl is azetidinyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, oxazepanyl, dihydroindolyl, dihydrofuryl, dihydroimidazolinyl, dihydrooxazolyl, tetrahydropyridinyl, dihydropyranyl, dihydrobenzofuranyl, benzodioxolyl, or benzodioxanyl.

In the present invention, $R_1$, $R_2$, and $R_3$ may be a substituent selected from the group consisting of, but are not limited to:

$R_1$: $C_{1-6}$ alkyl; and $R_2$ and $R_3$: a hydrogen atom, aryl,

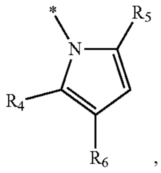
,
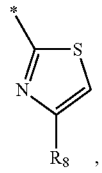
, or
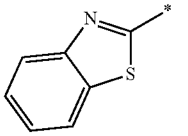

(in which $R_2$ and $R_3$ are the same as or different from each other, $R_4$ and $R_5$ are the same as or different from each other and are $C_{1-6}$ alkyl;

$R_6$ is

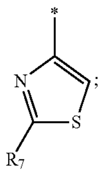

$R_7$ is $C_{1-6}$ alkylamino, or substituted or unsubstituted arylamino;

$R_8$ is $C_{1-6}$ alkyl or

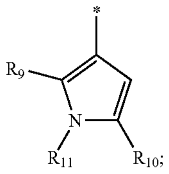

and $R_9$ to $R_{11}$ are $C_{1-6}$ alkyl or arylalkyl).

In the above substituents, * represents a position bound to the backbone of Chemical Formula 1.

Preferably, $R_1$, $R_2$, and $R_3$ are a substituent selected from the group consisting of, but are not limited to:

$R_1$: $C_{1-6}$ alkyl; and $R_2$ and $R_3$: a hydrogen atom, aryl,

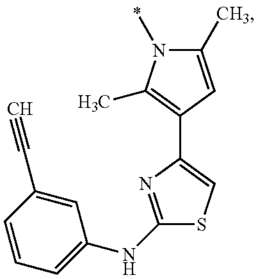
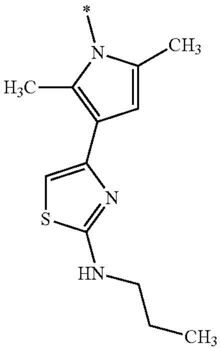
,
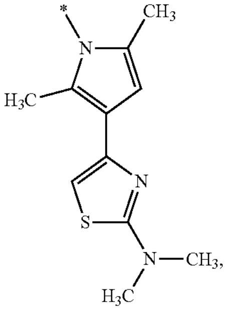
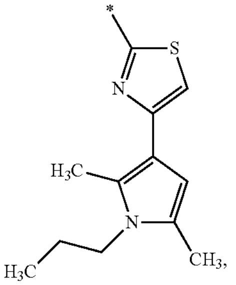

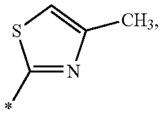
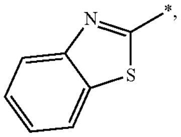
, or

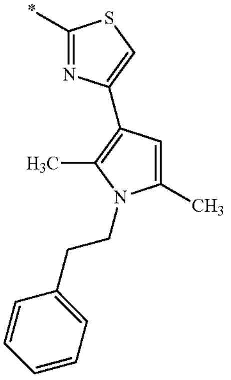

(in which $R_2$ and $R_3$ are the same as or different from each other).

In the above substituents, represents a position bound to the backbone of Chemical Formula 1.

More preferably, the compound represented by Chemical Formula 1 is any one compound selected from the group consisting of Chemical Formula 1-1 to Chemical Formula 1-7 below, but is not limited thereto.

[Chemical Formula 1-1]
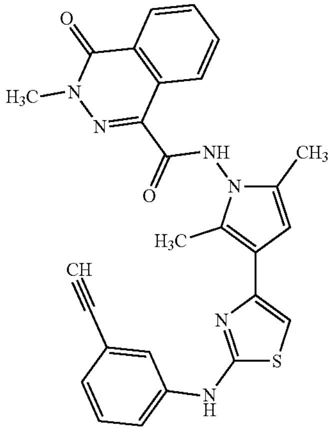
[Chemical Formula 1-2]
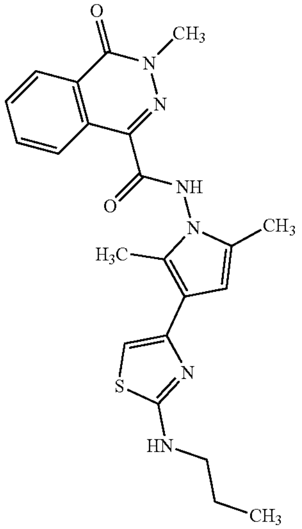
[Chemical Formula 1-3]
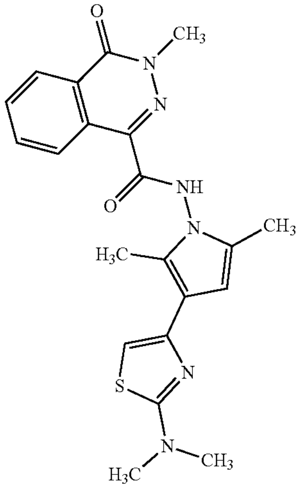
-continued
[Chemical Formula 1-4]
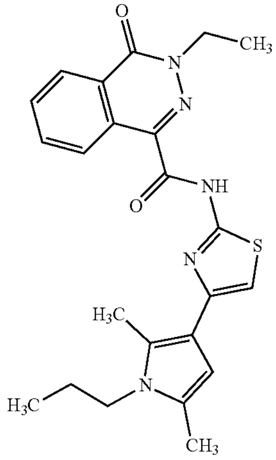
[Chemical Formula 1-5]
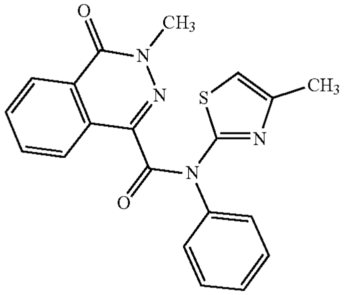
[Chemical Formula 1-6]
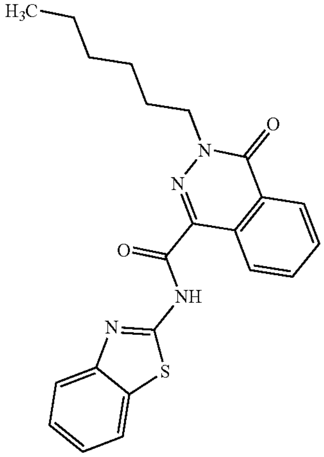

-continued

[Chemical Formula 1-7]

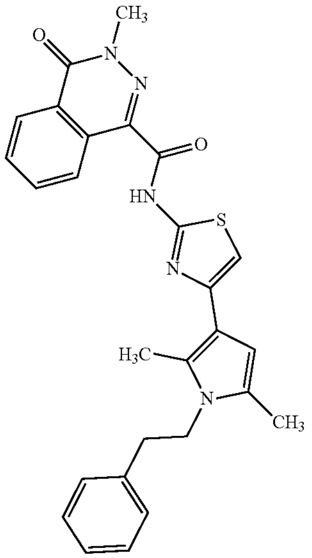

In the present specification, the compound of Chemical Formula 1-1 is named TIM1, the compound of Chemical Formula 1-2 is named TIM1c, the compound of Chemical Formula 1-3 is named TIM1d, the compound of Chemical Formula 1-4 is named TIM1-7, The compound of Chemical Formula 1-5 is named TIM1-10, the compound of Chemical Formula 1-6 is named TIM1-11, and the compound of Chemical Formula 1-7 is named TIM1-14 (Table 1).

TABLE 1

SMILES strings, IUPAC names, and molecular weights of active ligands

| Name | SMILES | IUPAC Name | MW (g/mol) |
|---|---|---|---|
| TIM1 | Cc1cc (-c2csc(Nc3cccc(c3)C#C) n2)c(C)n1NC(=O)c1nn(C) c (=O)c2ccccc12 | N-(3-{2-[(3-ethynylphenyl)amino]-1,3-thiazol-4-yl}-2,5-dimethylpyrrol-1-yl)-3-methyl-4-oxophthalazine-1-carboxamide | 494.57 |
| TIM1c | Cl.CCCNc1nc(cs1)-c1cc(C)n(NC(=O)c2nn(C) c(=O)c3ccccc23)c1C | N-{2,5-dimethyl-3-[2 -(propylamino)-1,3-thiazol-4-yl]pyrrol-l-yl}-3-methyl-4-oxophthalazine-1-carboxamide hydrochloride | 472.99 |
| TIM1d | CN(C)c1nc(csl)-c1cc(C)n(NC(=O)c2nn(C) c(=O)c3ccccc23)c1C | N-{3-[2-(dimethylamino)-1,3-thiazol-4-yl]-2,5-dimethylpyrrol-1-yl}-3-methyl-4-oxophthalazine-1-carboxamide | 422.51 |
| TIM1-7 | CCCn1c(C)cc (-c2csc(NC(=O)c3nn(CC)c (=O)c4ccccc34)n2)c1C | N-[4-(2,5-dimethyl-1-propylpyrrol-3-yl)-1,3-thiazol-2-yl]-3-ethyl-4-oxophthalazine-1-carboxamide | 435.55 |
| TIM1-10 | Cc1csc(n1)N(C(=O)c1nn (C)c(=O)c2ccccc12)c1c cccc1 | 3-methyl-N-(4-methy1-1,3-thiazol-2-yl)-4-oxo-N-phenylphthalazine-1-carboxamide | 376.43 |
| TIM1-11 | CCCCCCn1nc(C(=O)Nc2nc 3ccccc3s2)c2ccccc2c1=O | N-(1,3-benzothiazol-2-yl)-3-hexyl-4-oxophthalazine-1-carboxamide | 406.5 |
| TIM1-14 | Cc1cc (-c2csc(NC(=O)c3nn(C)c (=O)c4ccccc34)n2)c(C)n 1CCc1ccccc1 | N-{4-[2,5-dimethyl-1-(2 -phenylethyl)pyrrol-3-yl]-1,3-thiazol-2-yl}-3-methyl-4-oxophthalazine-1-carboxamide | 483.59 |

In the present invention, the compound exhibiting the TNF-α inhibitory effect preferably has the structure represented by Chemical Formula 1-1 or Chemical Formula 1-2, but is not limited thereto.

In another aspect, the present invention is directed to a composition for inhibiting TNF-α comprising the compound represented by Chemical Formula 1 or the pharmaceutically acceptable salt thereof.

In the present invention, the compound of Chemical Formula 1 inhibits the formation of a TNF-α homotrimer by specifically binding to the binding cavity of a TNF-α homodimer.

In an embodiment of the present invention, it has been confirmed that the compound inactivates the function of TNF-α by disrupting the TNF-α homotrimerization assembly, and also prevents binding to the TNF receptor.

In an embodiment of the present invention, it has been confirmed that the compound exhibits low cytotoxicity and a high attenuation effect in TNF-α-induced cell death, and also that the compound performs inhibition of activity of NF-κB and MAPKs, inhibition of caspase 3- and 8-dependent proapoptotic pathways, and inhibition of IL-6 (interleukin 6) and IL-8 secretion.

In the present invention, "tumor necrosis factor alpha (TNF-α)" is a cell-signaling protein (cytokine) involved in systemic inflammation, and is one of the cytokines that forms an acute phase reaction. TNF-α may be produced by many cell types such as CD4+ lymphocytes, NK cells, neutrophils, mast cells, eosinophils, and neurons, and is mainly produced by activated macrophages. TNF-α belongs to the TNF superfamily, which is composed of various transmembrane proteins having homologous TNF domains. TNF is able to bind to two receptors: TNFR1 (TNF receptor 1; CD120a; p55/60) and TNFR2 (TNF receptor 2; CD120b; p75/80). TNFR1 is expressed in most tissues, and may be fully activated by membrane-bound and soluble trimeric forms of TNF, whereas TNFR2 is typically found in cells of the immune system and responds to TNF homotrimers in membrane-bound form. TNF activates NF-κB and MAPKs, induces death signaling, and promotes inflammatory responses.

As used herein, the term "inhibiting" or "inhibition" refers to a phenomenon by which biological activity or action is deteriorated due to deficiency, disharmony, or any of a large number of other causes, and may include partial or complete blocking, reduction or prevention of activity of TNF-α, delaying of activation, inactivation, or downregulation.

As used herein, the term "inhibitor" refers to a molecule that partially or completely inhibits the effect of another molecule, such as a receptor or intracellular mediator, by any mechanism.

As used herein, the term "TNF-α inhibitor" or "composition for inhibiting TNF-α" refers to a material capable of directly, indirectly, or substantially interfering with, reducing, or inhibiting the biological activity of TNF-α.

The compound according to the present invention may be used in the form of a pharmaceutically acceptable salt, and the salt thereof is an acid addition salt formed by a pharmaceutically acceptable free acid. The free acid may include an inorganic acid or an organic acid, examples of the inorganic acid including hydrochloric acid, hydrobromic acid, sulfuric acid, phosphoric acid, and the like, and examples of the organic acid including citric acid, acetic acid, lactic acid, maleic acid, fumaric acid, gluconic acid, methanesulfonic acid, glycolic acid, succinic acid, tartaric acid, 4-toluenesulfonic acid, galacturonic acid, embonic acid, glutamic acid, aspartic acid, and the like.

The compound according to the present invention comprises all salts, hydrates, and solvates that may be prepared through typical methods, in addition to pharmaceutically acceptable salts.

Moreover, the compound according to the present invention may be prepared in a crystalline form or an amorphous form, and when the compound of Chemical Formula 1 is prepared in a crystalline form, it may optionally be hydrated or solvated.

Still another aspect, the present invention is directed to a composition for preventing or treating an autoimmune disease and/or an inflammatory disease comprising the composition for inhibiting TNF-α.

In the present invention, the autoimmune disease and/or the inflammatory disease may be selected from the group consisting of rheumatoid arthritis, psoriasis, psoriatic arthritis, Crohn's disease, juvenile idiopathic arthritis, spondyloarthritis, Behcet's disease, uveitis, plaque psoriasis, axial spondyloarthritis, ulcerative colitis, hidradenitis suppurativa, insulin-dependent diabetes mellitus, eczema, allergies, atopic dermatitis, acne, atopic rhinitis, pulmonary inflammation, allergic dermatitis, chronic sinusitis, contact dermatitis, seborrheic dermatitis, gastritis, gout, gouty arthritis, ulcers, chronic bronchitis, ulcerative colitis, ankylosing spondylitis, sepsis, angiitis, bursitis, temporal arteritis, solid cancers, Alzheimer's disease, arteriosclerosis, obesity, and viral infection, but not limited to.

As used herein, the term "autoimmune disease" refers to a disease that is caused when the internal immune system of the human body attacks normal internal cells rather than external antigens. Examples of autoimmune diseases include, but are not limited to, type 1 diabetes mellitus (insulin-dependent), systemic lupus, Crohn's disease, psoriasis, and the like, as well as rheumatoid arthritis.

As used herein, the term "inflammatory disease" refers to a disease that is caused by an inflammatory material (inflammatory cytokine) such as TNF-α, IL-1, IL-6, prostaglandin, leukotriene, or NO secreted from immune cells such as macrophages due to excessive stimulation of the immune system by harmful stimuli such as inflammatory factors or radiation.

As used herein, the term "prevention" refers to any action that suppresses or delays an autoimmune disease and/or an inflammatory disease through administration of a pharmaceutical composition comprising the compound or the pharmaceutically acceptable salt thereof. In addition, as used herein, the term "treatment" refers to any action that ameliorates or eliminates symptoms of an autoimmune disease and/or an inflammatory disease through administration of a pharmaceutical composition comprising the compound represented by Chemical Formula 1 or the pharmaceutically acceptable salt thereof.

The composition for preventing or treating an autoimmune disease and/or an inflammatory disease according to the present invention may comprise the compound represented by Chemical Formula 1 alone in a pharmaceutically effective amount, or may comprise at least one pharmaceutically acceptable carrier, excipient, or diluent. Here, the pharmaceutically effective amount is an amount sufficient to prevent, ameliorate, or eliminate symptoms of an autoimmune disease and/or an inflammatory disease.

"Pharmaceutically acceptable" means that a material is physiologically acceptable and does not usually cause allergic reactions such as gastrointestinal disorders and dizziness or reactions similar thereto when administered to humans. Examples of the carrier, excipient, or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methylhydroxybenzoate, propylhydroxybenzoate, talc, magnesium stearate, and mineral oil. In addition, fillers, anti-aggregation agents, lubricants, wetting agents, fragrances, emulsifiers, and preservatives may be further comprised.

In addition, the pharmaceutical composition according to the present invention may comprise at least one known active ingredient having a therapeutic effect on an autoimmune disease or inflammatory disease, in addition to the compound represented by Chemical Formula 1.

The pharmaceutical composition according to the present invention may be formulated using methods known in the art so as to provide rapid, sustained, or delayed release of an active ingredient after administration to a mammal other than a human. Formulations may take the form of powders, granules, tablets, emulsions, syrups, aerosols, soft or hard gelatin capsules, sterile injectable solutions, or sterile powders.

The pharmaceutical composition according to the present invention may be administered through various routes including oral, transdermal, subcutaneous, intravenous, or intramuscular routes, and the dosage of the active ingredient may be appropriately selected depending on various factors such as the route of administration, the age, gender, and body weight of a patient, the severity of disease, etc., and the composition for preventing or treating an autoimmune disease and/or an inflammatory disease according to the present invention may be administered in combination with a known compound having an effect of preventing, ameliorating or eliminating symptoms of inflammatory diseases.

Yet another aspect, the present invention is directed to a method of preventing or treating an autoimmune disease and/or an inflammatory disease comprising administering the composition for inhibiting TNF-α.

Still yet another aspect, the present invention is directed to the use of the composition for inhibiting TNF-α for the prevention or treatment of an autoimmune disease and/or an inflammatory disease.

A further aspect, the present invention is directed to the use of the composition for inhibiting TNF-α for the manufacture of a medicament for the prevention or treatment of an autoimmune disease and/or an inflammatory disease.

Since the above-described "composition for inhibiting TNF-α" is employed in the prevention or treatment method and the use according to the present invention, redundant descriptions thereof will be omitted.

A better understanding of the present invention may be obtained through the following examples. These examples are merely set forth to illustrate the present invention, and are not to be construed as limiting the scope of the present invention, as will be apparent to those of ordinary skill in the art.

Example 1: Materials and Methods

Example 1-1: Preparation of Cell Lines and Reagents

HDF (ATCC, Manassas, VA, USA) and L929 cell lines (ATCC) were maintained in high-glucose Dulbecco's modified Eagle's medium (DMEM) (Thermo Fisher Scientific, Inc., Waltham, MA, USA) containing a 0.2% normocin solution (InvivoGen, San Diego, CA, USA), 1% penicillin/streptomycin solution, and 10% fetal bovine serum (FBS). Both cell lines were incubated in a humidified atmosphere containing 5% of $CO_2$ at 37° C. (Thermo Fisher Scientific, Inc.). SPD304 (MolPort ID: MolPort-042-665-817; ChemDiv catalog #4031-0592), C87 (Tocris Cookson, Bristol, UK), rhTNF-α (Miltenyi Biotec, Auburn, California, USA), rhTNF-α (Miltenyi Biotec), act-D (Thermo Fisher Scientific, Inc.), and BS3 (Thermo Fisher Scientific, Inc.) were purchased from the respective companies, noted in parentheses above. All hit ligands were dissolved in absolute dimethyl sulfoxide (DMSO).

Example 1-2: Animals

Male DBA/1J mice (20-23 g) were purchased from Central Lab. Animal Inc. (Seoul, Korea). Animals were housed in a limited-access rodent facility with a maximum of 4 animals per polycarbonate cage, with free access to pelleted food and water. The temperature was maintained at 22-24° C. with a 12/12-hour light/dark cycle. Animals were acclimatized for at least 1 week prior to starting the experiment. The number of animals used per experiment or test and the potential suffering were minimized. All methods were approved by the Animal Care and Use Committee of Kyung-Hee University, Korea. All procedures were executed in accordance to the Guide for the Care and Use of Laboratory Animals by the Korea National Institute of Health.

Example 1-3: Collagen-Induced Mouse Polyarthritis and Experimental Groups

Figure 10:
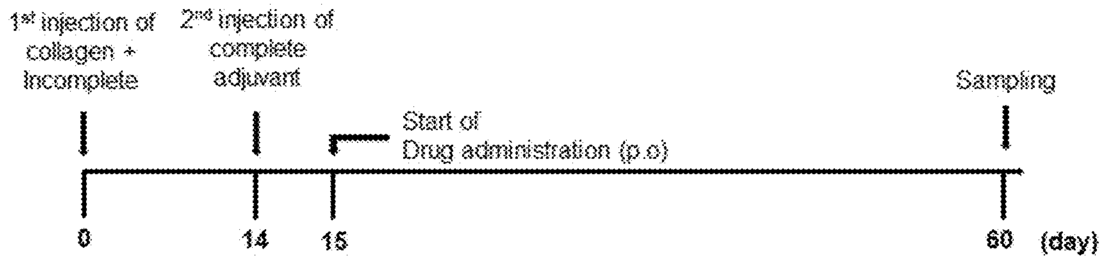
FIG. 10 shows the experimental schedule for developing a mouse model of collagen-induced arthritis.

Male DBA/1J mice (6-week-old) were subcutaneously injected with 50 μl of an emulsion containing 100 μg of chicken collagen type II (Sigma-Aldrich Co., St. Louis, MO, USA) dissolved in 25 μl of acetic acid and 25 μl of a complete Freund's adjuvant (Sigma-Aldrich Co.) at the base of the tail thereof, and the day of the first immunization was defined as day 0. On Day 14, the mice were injected with a booster of 50 μl of the emulsion having the same composition as the first immunization, except that an incomplete Freund's adjuvant was used. The experimental schedule for developing a mouse model of collagen-induced arthritis (CIA) is shown in FIG. 10. All mice were randomly divided into 4 experimental groups: non-treated normal group (NOR, n=4), collagen-injected and vehicle-treated arthritis control group (CIA, n=4), 2 mg/kg TIM1c-treated arthritis group (TIM1c 2 mg/ml, n=4), and 20 mg/kg TIM1c-treated arthritis group (TIM1c 20 mg/ml, n=5). The treatment groups were orally fed 2 or 20 mg/kg of TIM1c every 2 days from day 15 to day 60 after the first immunization.

Example 1-4: Behavioral Assessment of Arthritis Symptoms

In order to evaluate the progression of arthritis in CIA mice, four parameters (body weight, paw volume increase, squeaking score, and arthritis score) were measured after the first immunization with collagen and complete Freund's adjuvant. The body weights of the mice were measured using a digital balance (Mettler-Toledo Inc., Columbus, OH, USA). In order to assess nociception and hyperalgesia, ankle pain was evaluated on a scale measuring squeaking. Squeaking included any vocalization evoked by ankle flexion and extension. The flexion and extension procedures were repeated 10 times every 5 seconds, and the mouse was rated 0 (no vocalization) or 1 (vocalization) for each hindlimb thereof. The total number of vocalizations detected by the observer was counted as the number of squeaks. Paw swelling was measured by volume displacement of an electrolyte solution using a water-displacement plethysmometer (Ugo-Basil Biological Research Apparatus Co., Comerio-Varese, Italy), as previously described (Bang J. S. et al. (2009) *Arthritis Res. Ther.* 11(2):R49). The hindlimbs were immersed to the line of the hairy skin, and the volumes thereof were read on a digital display. The increase in paw volume was represented compared to day 0, which was defined as zero. The arthritis index was assessed by grading the apparent arthritis severity in all joints of each limb using a per-limb 4-point scale; a maximum score of 16 for each mouse, 0=neither erythema nor swelling of any joint in one limb, 1=erythema or swelling of at least one joint per limb, 2=erythema or swelling of fewer than 3 joints per limb, 3=erythema or swelling of all joints in one limb, 4=ankylosis and deformity of all joints in one limb.

Example 1-5: Cell Viability Assay

In order to measure cell viability, a colorimetric 1-(4,5-dimethylthiazol-2-yl)-3,5-diphenylformazan (MTT) assay (Sigma-Aldrich Co.) was performed. HDFs were seeded at a density of $10^4$/well in 96-well plates (BD Biosciences, San Jose, CA, USA), grown overnight, and then treated with a test compound at various concentrations for 24 hours. The next day, the medium was replaced with a medium (100 μl/well) containing a 10% MTT solution, followed by incubated at 37° C. for 3 hours. This solution was replaced with DMSO (100 μl/well), and the plates were incubated at room temperature for 30 minutes. Thereafter, the plates were read at a wavelength of 540 nm using a microplate spectrophotometer system (Molecular Devices, Silicon Valley, California).

Example 1-6: IL-8 and IL-6 Cytokine Detection Assays

HDFs were seeded at a density of $10^4$/well in a 96-well plate (BD Biosciences) and grown overnight. The cells were treated for 24 hours with a 1-hour-pre-incubated mixture of rhTNF-α and test compounds. IL-8 secretion was assessed by a human IL-8 uncoated ELISA kit (eBioscience, Inc., San Diego, CA, USA), and IL-6 secretion level was assessed by a human IL-6 ELISA MAX™ Deluxe kit (BioLegend, San Diego, CA, USA). The microtiter plates were then analyzed at an appropriate wavelength using a microplate spectrophotometer system (Molecular Devices, Silicon Valley, California).

Example 1-7: Cell Death Attenuation Assay

HDFs ($10^4$/well) and L929 cell lines ($1.5\times10^4$/well) were seeded in 96-well plates and grown overnight under appropriate conditions. The next day, HDFs and L929 cells were pretreated with 1 μg/ml act-D and 0.1 μg/ml act-D, respectively, followed by incubated for 30 minutes. Thereafter, a 1-hour-preincubated mixture of 10 ng/ml rhTNFα with test compounds or 1 ng/ml rmTNFα with test compounds, was applied to HDFs and L929 cells, respectively. The cells were incubated for 24 hours post-treatment, and survival was measured by the MTT assay. Cell viability was calculated with reference to the no-treatment control group. The obtained values were normalized with respect to the act-D treatment group and then used to calculate death attenuation (%) rate using the following equation:

$$\text{Death attenuation}(\%) = 100 - \left(\frac{100 - \text{sample value}}{100 - ActD\ \&TNF\alpha\ \text{cotreatment value}} * 100\right)$$

Images of the treated wells were captured using an inverted microscope (OLYMPUS IX53™; Olympus Corporation, Tokyo, Japan).

Example 1-8: Western Blot Analysis

Total protein was extracted from the treated cells using an M-PER mammalian protein extraction reagent (Thermo Fisher Scientific, Inc.). The cell pellets were dissolved in a mixture of M-PER with protease and phosphatase inhibitor cocktail (Thermo Fisher Scientific, Inc.) at 4° C. for 1 minute, and the lysate thus obtained was centrifuged at 16,000×g and 4° C. for 10 minutes. The supernatant containing the protein was collected in a separate Eppendorf tube, and a BCA assay (Sigma-Aldrich) was performed for protein quantification. 20 Hg of a protein sample was placed in a 10-12% polyacrylamide gel (containing SDS), and the separated protein was transferred to a nitrocellulose membrane (HYBOND ECL™; Amersham Pharmacia Biotech Inc, Piscataway, New Jersey) of a mini-PROTEAN tetra cell and mini trans-blot electrophoretic transfer cell system (Bio-Rad Laboratories). Membrane blocking was performed with 5% nonfat dried milk for 1 hour. The membrane was subjected to immunoblotting through gentle shaking overnight at a temperature of 4° C. with certain primary antibodies, i.e. antibodies to (phospho-)p-p65, p-JNK, JNK, p-ERK, ERK, cleaved caspase 3 (Cell Signaling Technology Inc., Danvers, MA, USA), p-p38, caspase 8, and β-actin (Santa Cruz Biotechnology Inc., Dallas, TX, USA). The next day, after rigorous washing with PBST, the membrane was incubated with peroxidase-conjugated anti-mouse or anti-rabbit IgG antibodies at room temperature for 2 hours. Protein was detected using a SuperSignal West Pico ECL solution (Thermo Fisher Scientific, Inc.) and visualized with a CHEMIDOC™ Touch Imaging System (Bio-Rad Laboratories).

Example 1-9: Dissociation of TNF-α Trimerization Assembly

Inhibitors were incubated with 100 ng of recombinant TNF-α at 37° C. for 1 hour and then cross-linked with 4.8 mM BS3 (Thermo Fisher Scientific, Inc.) at room temperature for 30 minutes. Then, a 1/10 volume of 1 M Tris-HCl (pH 7.5) was added to stop the reaction. Thereafter, samples were separated by SDS-PAGE, followed by Western blotting with anti-TNF-α antibody (Cell Signaling Technology Inc.).

Example 1-10: Preparation of Ligand Library

A screening library was constructed using chemical structures provided by ZINC (druglike and leadlike) and different vendors (FIGS. 1A to 1D and Table 2). Chemical structures were prepared using the sdwash tool of Molecular Operating Environment (MOE) software (2013.08; Chemical Computing Group ULC, 1010 Sherbooke St. West, Suite #910, Montreal, QC, Canada, H3A 2R7, 2017). The ligand structures were cleaned up by removing disconnected salt atoms and inorganic metal ions as well as ligands having reactive groups. For ligands having broken fragments, only the largest fragments were kept. Explicit hydrogen atoms were added, and the protonation state was adjusted by protonating the strong base and deprotonating the strong acid. A maximum of 10 tautomeric states were listed for each ligand, and intramolecular bonds were scaled to the appropriate length. The resulting structures were subjected to energy minimization using the MMFF94x force field until a root mean square gradient of 0.1 was reached. Partial charges were calculated on the ligand atoms before energy minimization with the MMFF94x force field.

Example 1-11: Calculation of Molecular-Fingerprint-Based Ligand Similarity

In order to emphasize molecular properties, molecular fingerprints were calculated for each ligand in a database according to a bit-packed MACCS Structural Keys (FP: BIT_MACCS) scheme. In order to identify ligands that are at least 60-80% similar to those selected from among the known set of TNF-α inhibitors reported in the literature, an in-house support vector language (SVL) script was applied. The search was performed using a Tanimoto similarity metric called the Tanimoto coefficient, which measures the similarity between two fingerprints through the expression #AB/(#A+#B−#AB). Here, A and B are two fingerprints, and #represents the number of features. The resultant ligands were stored in a separate library for subsequent screening.

Example 1-12: Pharmacophore Model Creation

Pharmacophore models were established based on two inhibitors, JNJ525 and SPD304, and screening for each ligand was performed. Pharmacophore features were created around essential ligand groups using a planar-polar-charged-hydrophobic scheme. Based on the observed interactions with TNF-α residues, four pharmacophore features were created on each of the ligands. The resultant hits were kept in a different library for structure-based virtual screening.

Example 1-13: Virtual Screening

Two separate virtual screenings were performed, one using the TNF-α/SPD304 complex (PDB ID: 2AZ5) and the other using the TNF-α/JNJ525 complex (PFB ID: 5MU8). The TNF-α atom remained rigid, but the ligand atom was flexible. Docking was performed with the triangle-matcher placement method and the London dG scoring function, maintaining a maximum of 30 docked poses for each ligand. The top-scoring poses for each ligand were applied to another round of docking run with MMFF94x force field refinement and Affinity dG scoring function to thus maintain 30 docked conformations of each ligand. At the final step, the resultant ligands were screened based on the electron density of original ligand in the TNF-α cavity.

Example 1-14: In Silico (Computer Programming in Virtual Experiment) Toxicity Prediction For the top 100 ligands having the highest scores in the library of virtual screening hits, toxicity was predicted in silico using open-source tools such as ProTox (Banerjee P. et al. (2018) *Nucleic Acids Res.* 46(W1):W257-W263), TEST (U.S. Environmental Protection Agency, Washington, DC), Datawarrior (Sander T. et al. (2015) *J. Chem. Inf. Model* 55(2):460-473), and PAINS-Remover (Baell J. B. & Holloway G. A. (2010) *J. Med. Chem.* 53(7): 2719-2740). The top 10 ligands without any toxic fragments were purchased for experimental validation of anti-TNF activity thereof.

Example 1-15: MD Simulation of TNF-α-SPD304 or TNF-α-JNJ525 Complex

The crystal structure of TNF-α complexed with SPD304 and JNJ525 was obtained from PDB. The topology of the ligand was obtained from an automated topology builder (ATB 3.0) server (Stroet M. et al. (2018) *J. Chem. Theory Comput.* 14(11):5834-5845). Energy minimization and MD simulation were performed using the gromos96-54a6 force field in GROMACS 5.1.5 software (Abraham M. J. et al. (2015) *SoftwareX* 1-2:19-25). Protein-ligand complexes were embedded in cubic boxes with a distance of 20 Å between the surface thereof and the box boundary. A simple point-charge (SPC216) water molecule and an appropriate amount of counterion were added to the simulation box to neutralize the total charge of the simulation system. Energy minimization was performed through the steepest-descent algorithm until a maximum force of 1000 $kJmol^{-1}$ $nm^{-1}$ was reached. The temperature of the simulation system was equilibrated according to the V-rescale scheme, which is a modified version of the Berendsen temperature-coupling scheme. Pressure equilibration was achieved using the Parinello-Rahman algorithm at 1 bar. During the temperature and pressure equilibration process, the backbone heavy atom of the protein was harmonically suppressed for 100 ps. The production run was performed for 100 ns with no positional restrictions on the backbone atoms. Period-boundary conditions were applied to the simulation system, and all bonds including hydrogen atoms were limited using a linear constraint solver algorithm. A timestamp of 0.002 ps was used, and trajectory snapshots were saved every 10 ps. Data analysis was performed using VMD (Humphrey W., Dalke A. & Schulten K. (1996) *J. Mol. Graph* 14(1):33-38, 27-38), PyMOL (Schrodinger, LLC, New York, NY, USA), discovery studio 4.0 (Dassault Systems, San Diego, CA, USA), MOE software, and built-in tools of the GROMACS program.

Example 1-16: Identification of Structural Derivatives of TIM1

In order to improve the activity of TIM1, the TIM1 structure was used, and the Tanimoto metrics cutoff was set to 0.8 (i.e. 80% similarity cutoff), so a similarity search was performed in the MolPort database (URL: www.molport-.com/shop/index). A total of 100 derivatives were selected as SDF files for in silico docking in MOE. The ligands were washed and subjected to energy minimization using the sdwash protocol of MOE. Molecular docking was performed at the SPD304-binding site of TNF-α (PDB ID: 2AZ5), and docked poses were ranked based on the binding affinity score (S score). After rescoring with MMFF94x force field refinement and Affinity dG scoring function, ligands showing greater affinity than TIM1 were selected for experimental validation.

Example 1-17: MD Simulation of TNF-α-TIM1 or TNF-α-TIM1c Complex

In order to analyze the intermolecular interactions under dynamic conditions, rounds of 100 ns MD simulations were performed on the complex between TNF-α and TIM1 or a potent derivative thereof. Ligand topology was obtained using an ATB 3.0 server, and MD simulation was performed using the same parameters as described above.

Example 1-18: Construction of Free Energy Landscape (FEL)

FEL was constructed to extract the lowest energy conformation of ligand-bound TNF-α used in virtual screening. Cluster analysis was performed for each MD trajectory, and FELs for all conformations from the largest cluster were calculated. The FEL values were calculated using the gmx sham tool from GROMACS, and plots were generated using the demo version of Mathematica software (version 11.2; Wolfram Research, Inc., Champaign, IL, USA). A representative low-energy conformation was extracted from the FEL for docking or visual presentation.

Example 1-19: Computation of Binding Free Energy

The binding affinity of the TNF-α-ligand complex was calculated through a molecular mechanics Poisson-Boltzmann surface area calculation method. Calculation was performed for all conformations between 90 and 100 ns MD trajectories in g_mmpbsa software (Kumari R., Kumar R., Open-Source Drug Discovery C, & Lynn A (2014) g_mmpbsa—a GROMACS tool for high-throughput MM-PBSA calculations. *J. Chem. Inf. Model* 54(7):1951-1962) using Equation 1 below.

$$\Delta G_{bind} = \langle G_{complex} \rangle - \langle G_{protein} \rangle - \langle G_{ligand} \rangle \quad \text{(Equation 1)}$$

Here, $G_{bind}$ is the total binding free energy, and $G_{complex}$, $G_{protein}$ and $G_{ligand}$ are the average free energy values of the complex, protein, and ligand, respectively.

The free energy of each component was calculated using Equation 2 below.

$$G = G_{bond} + G_{ele} + G_{vdW} + G_{pol} + G_{npol} - TS \quad \text{(Equation 2)}$$

Here, $G_{bond}$ is the sum of binding, angular, and dihedral energy values, and $G_{ele}$ and $G_{vdW}$ are, respectively, electrostatic energy and vdW energy derived from the calculation of molecular mechanics energy. $G_{pol}$ and $G_{npol}$ respectively represent the polar and non-polar contributions to the solvation energy. $G_{pol}$ was obtained by solving the Poisson-Boltzmann equation, and $G_{npol}$ was estimated from the linear relationship with the solvent-accessible surface area. Configurational entropy (TS) is generally neglected because of the increased computational cost and overestimation of the binding free energy values.

Example 1-20: Statistical Analysis

All in vitro data analyses were performed using a two-tailed paired Student's t-test in Microsoft Excel 2016 or GraphPad Prism 7 software. All data are represented as mean±SEM. Statistical differences between animal groups were confirmed using two-way ANOVA followed by Bonferroni post-test correction (for multiple comparisons of body weight, squeaking score, paw volume increase, and arthritis index). P values<0.05 were considered to indicate statistical significance.

Example 2: Identification of TIM1 as Potential TNF-α Inhibitor

Identification of a novel TNF-α inhibitor, TIM1, was performed via an in silico approach using the crystal structure of the TNF-α-SPD304 complex (Protein Data Bank [PDB] ID: 2AZ5) and a multiconformational chemical library obtained from various sources (Table 2).

TABLE 2

Chemical compound libraries used in discovery of TNF-α inhibitor

| Compound library | No. of compounds |
|---|---|
| ZINC druglike | 14,480,911 |
| ZINC leadlike | 5,449,805 |
| Enamine | 3,005,135 |
| ChemBridge | 1,586,299 |
| ChemDiv | 1,912,842 |
| Life Chemicals | 497,067 |
| Maybridge | 70,780 |
| Total | 27,002,839 |

The ligands from the vendors are obtainable free from the ZINC interface (zinc.docking.org/).

Compounds having drug-like physicochemical properties were isolated through a fingerprint-based Tanimoto coefficient similarity metric using TNF-α inhibitors selected as query molecules (Table 3 and FIG. 1A).

TABLE 3

Ligands used to find drug-like properties in compound library through molecular fingerprints

| Inhibitor name | Target | Activity | Reference |
|---|---|---|---|
| SPD304 | TNF-α | $IC_{50}$ = 22 μM | He M. M. et al. (2005) Small-molecule inhibition of TNF-alpha. *Science* 310 (5750): 1022-1025 |

TABLE 3-continued

Ligands used to find drug-like properties in compound library through molecular fingerprints

| Inhibitor name | Target | Activity | Reference |
|---|---|---|---|
| Physcion-8-O-β-D-monoglucoside | TNFRI | $K_D$ = 376 nM | Cao Y. et al. (2016) Identification of a ligand for tumor necrosis factor receptor from Chinese herbs by combination of surface plasmon resonance biosensor and UPLC-MS. *Anal. Bioanal. Chem.* 408 (19): 5359-5367 |
| AP-906/41640035 | TNF-α | $IC_{50}$ = 14 μM | Shen Q. et al. (2014) Discovery of highly potent TNFalpha inhibitors using virtual screen. *Eur. J. Med.* Chem. 85: 119-126 |
| Quinuclidine 1 | TNF-α/TNFR1 interface | $IC_{50}$ ≈ 5 | μM | Chan D. S. et al. (2010) Structure-based discovery of natural-product-like TNF-alpha inhibitors. *Angew. Chem. Int. Ed. Engl.* 49 (16): 2860-2864 |
| Indolo-quinolizidine 2 | TNF-α/TNFR1 interface | $IC_{50}$ ≈ 10 | μM | |
| Japonicone A | TNF-α/TNFR1 interface | $IC_{50}$ ≈ 10 | μM | Hu Z. et al. (2012) Japonicone A antagonizes the activity of TNF-alpha by directly targeting this cytokine and selectively disrupting its interaction with TNF receptor-1. *Biochem. Pharmacol.* 84 (11): 1482-1491 |
| Inhibitor 1 | TNF-α | $IC_{50}$ = 10 μM | Choi H. et al. (2010) Discovery of the inhibitors of tumor necrosis factor alpha with structure-based virtual screening. *Bioorg. Med. Chem. Lett.* 20 (21) : 6195-6198 |
| C87 | TNF-α | IC50 = 8.73 μM | Ma L. et al. (2014) A novel small-molecule tumor necrosis factor alpha inhibitor attenuates inflammation in a hepatitis mouse model. *J Biol. Chem.* 289 (18): 12457-12466 |
| Erythrosine B | TNF-α/TNFR1 interface | IC50 = 5 μM | Ganesan L. et al. (2011) The food colorant erythrosine is a promiscuous protein-protein interaction inhibitor. *Biochem. Pharmacol.* 81(6): 810-818 |

TNF-α is tumor necrosis factor α, TNFR1 is tumor necrosis factor receptor 1, and TNF-α/TNFR1 interface indicates the surface of TNF-α that interacts with TNFR1.

Ligand libraries were screened using the pharmacophore model of the ligands SPD304 and JNJ525, having well-defined intermolecular interactions with TNF-α (Blevitt J. M. et al. (2017) *J. Med. Chem.* 60(8):3511-3517) (FIG. 1B and FIG. 1C). Then, a set of 15,668 ligands was subjected to structure-based virtual screening in the central hydrophobic cavity of the TNF-α homodimer. The docked ligand poses were graded using the MMFF94x force-field-based binding free energy (GBVI/WSA dG) score. In silico toxicity assay was performed on the 100 top-scoring ligands using online and offline computational tools, including removal of pan-assay interference (PAINS) compounds. The top 10 ligands without any toxic fragments in chemical structures were obtained for in vitro confirmation of bioactivity thereof.

The 10 chemicals thus obtained were initially tested for toxicity to human dermal fibroblasts (HDFs) at concentrations of 1-50 μM. After 24 hours of compound treatment, cell viability was monitored through a colorimetric 3-(4,5-dimethylthiazol-2-yl)-2,5-diphenyltetrazolium bromide (MTT) assay. Among the molecules tested, TIM1 (FIG. 1D) showed no cytotoxicity up to a concentration of 50 μM, whereas the other compounds showed mild toxicity to cells. It is noteworthy that the known TNF-α inhibitors SPD304 and C87, serving as positive controls, showed cytotoxicity in this experiment (FIG. 2A). TIM1 showed no lethality in HDF or murine fibrosarcoma cell line L929 up to 200 μM (FIGS. 8A and 8B). Based on the observed cytotoxicity of the compounds, TIM1 was selected for further experimentation to test the inhibitory effect of TNF-α-mediated cytokine secretion. HDFs were cultured with pre-cultured mixtures of recombinant human TNF-α (rhTNF-α) with TIM1 or SPD304, and for evaluation of cytokine secretion profiles through enzyme-linked immunosorbent assay (ELISA), the culture supernatant was collected after 24 hours. Thereby, it was confirmed that TIM1 inhibited TNF-α-mediated secretion of human interleukin 8 (hIL-8; FIG. 2B) and human interleukin 6 (hIL-6; FIG. 2C) in a concentration-dependent manner. The $IC_5O$ values of TIM1 for the secretion of hIL-8 and IL-6 were calculated to be 16.71 and 6.3 μM, respectively (FIG. 2D and FIG. 2E). Although the known anti-TNF ligand SPD304 completely inhibited the secretion of hIL-8 or hIL-6 at 50 μM, this significant inhibition was due to severe cytotoxicity at high concentrations (FIG. 2F). At lower concentrations (i.e. 10 μM), SPD304 was found to increase the secretion of cytokines. This is deemed to be due to the physiological stress that the cells experienced before ligand-induced necrosis (FIG. 2B and FIG. 2C) (Grootjans S. et al. (2017) *Cell Death Differ.* 24(7):1184-1195).

Figures 3A, 3B, 3C, 3D, 3E, 3F:
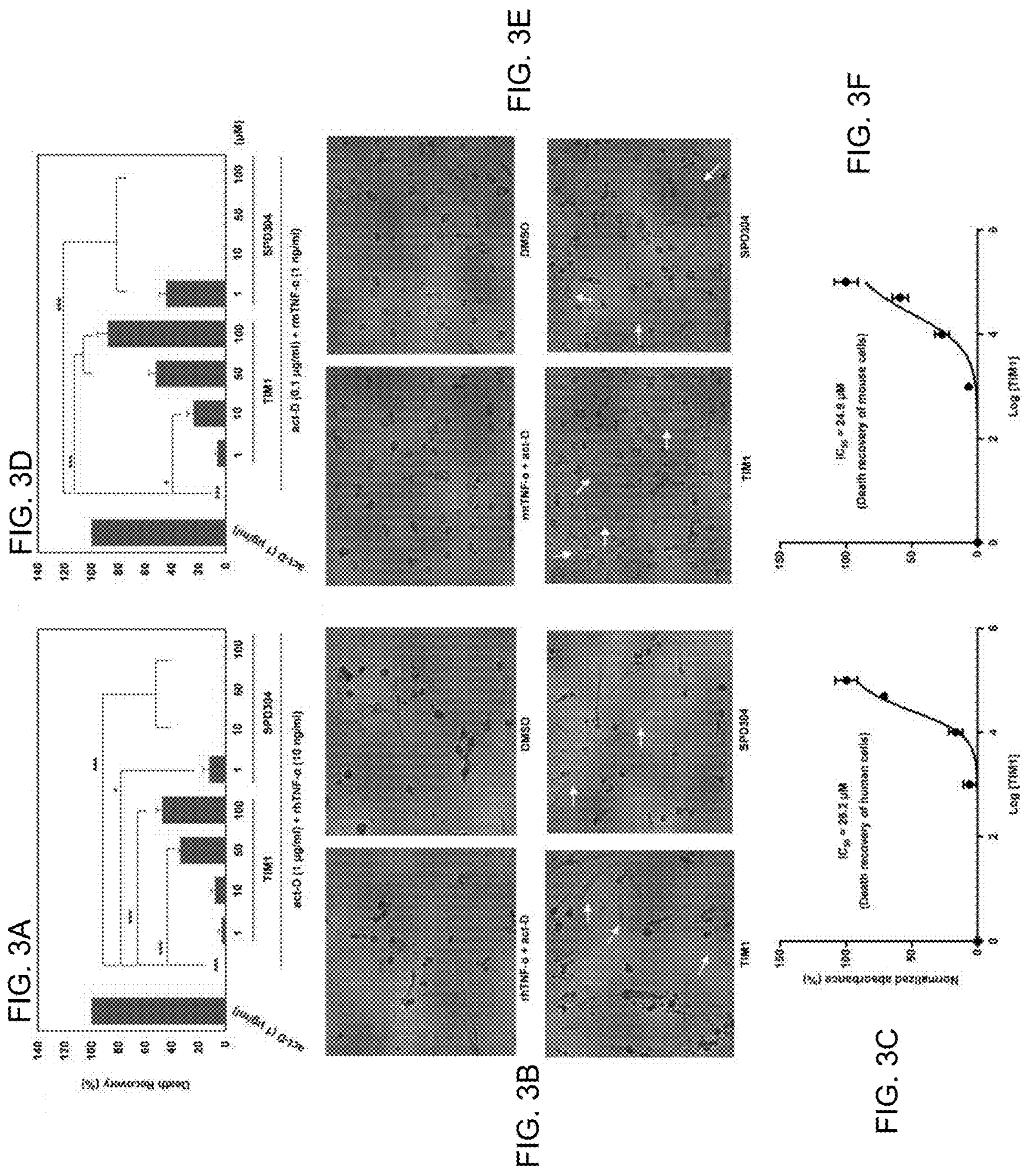
FIGS. 3A to 3F show the attenuation of tumor necrosis factor α (TNF-α)-induced cell death.

Example 3: Confirmation of Effect of TIM1 on Preventing TNF-α-Induced Death in Human and Mouse Cells TNF-α is a potent inducer of the death of inflammatory cells via activation of the TNFR1-associated death signaling pathway (Elinav E. et al. (2013) *Nat. Rev. Cancer* 13(11): 759-771). In order to evaluate the effect of TIM1 on preventing TNF-α-mediated apoptosis, different concentrations of TIM1 or SPD304 (pre-cultured with rhTNF-α) were applied to actinomycin D (act-D)-sensitized HDFs. Significant attenuation of TNF-α-induced apoptosis was observed upon TIM1 treatment (FIG. 3A and FIG. 3B), and the $IC_{50}$ value was 26.2 HM (FIG. 3C). On the other hand, similar effects were not exerted by the known anti-TNF compound SPD304 at concentrations higher than 1 μM. Next, in order to test whether TIM1 is able to reproduce the protective effect thereof in mouse cells, a pre-cultured mixture of TIM1 or SPD304 and recombinant mouse TNF-α (rmTNF-α) was applied to an act-D-sensitized L929 cell line. As expected, TIM1 inhibited the rmTNF-α-mediated proapoptotic pathway in L929 cells in a concentration-dependent manner (FIG. 3D and FIG. 3E), with an $IC_{50}$ value of 24.9 μM (FIG. 3F). In contrast, SPD304 did not reduce the death of these cells at concentrations other than 1 μM (FIG. 3D and FIG. 3E).

Figure 4A:
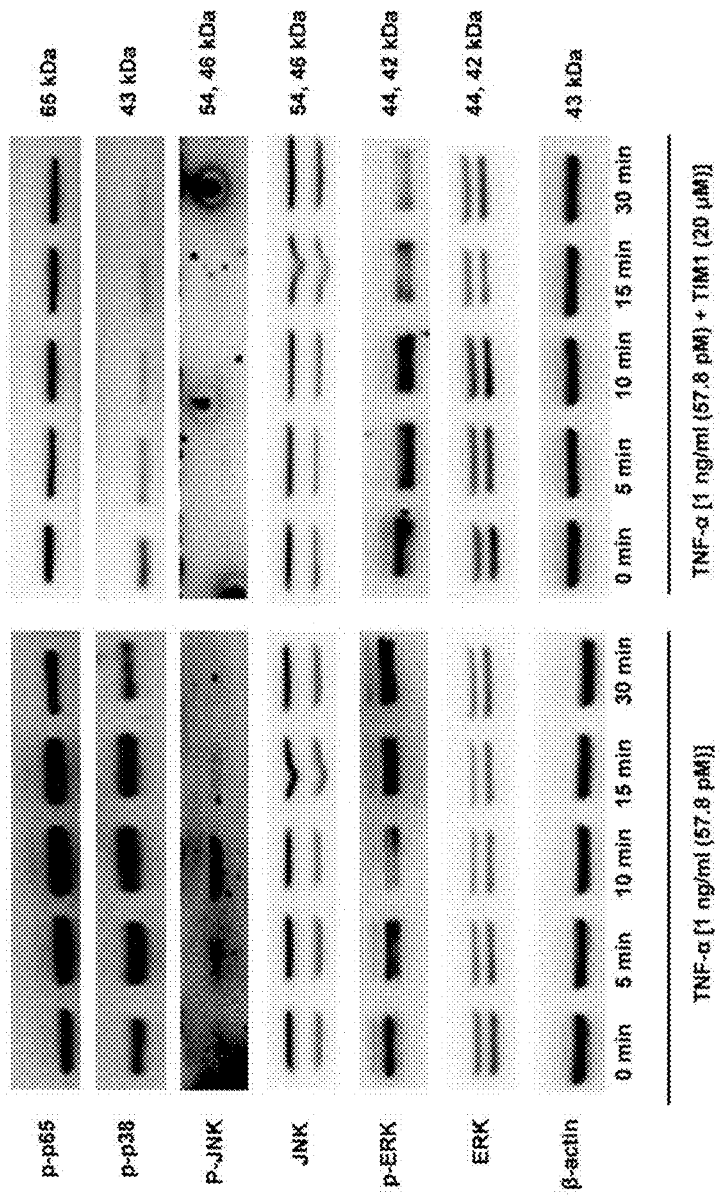
FIGS. 4A and 4B show inhibition of multiple tumor necrosis factor α (TNF-α)-dependent signaling pathways by TIM1.
Figure 4B:
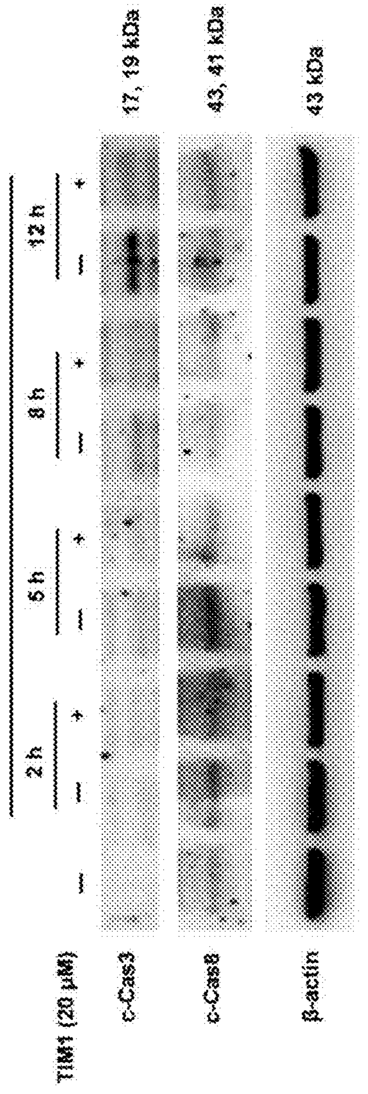

Example 4: Confirmation of Effect of TIM1 on Inhibiting TNF-α-Dependent Signaling Pathway Activation of TNFR1 by TNF-α triggers several distinct signaling pathways, including the NF-κB, MAPK, and caspase pathways (Brenner D., Blaser H. & Mak T. W. (2015) *Nat. Rev. Immunol.* 15(6): 362-374). The present inventors first evaluated the effect of TIM1 on phosphorylation of the p65 subunit, which is an essential indicator of NF-κB activation, in L929 cells through Western blotting (FIG. 4A). As shown in FIG. 4A, TNF-α-mediated phosphorylation of the p65 subunit was attenuated by TIM1 compared to untreated cells, in which the amount of phosphorylated p65 increased over time. Next, phosphorylation of MAPKs such as p38 MAPK, JNK, and ERK also appeared to be inhibited through treatment with TIM1. Moreover, TIM1 inhibited the activation of the caspase signaling pathway, a hallmark of programmed/inflammatory cell death (FIG. 4B). Specifically, TIM1 blocked the formation of cleaved active caspases 3 and 8 induced by TNF-α stimulation.

Figure 5B:
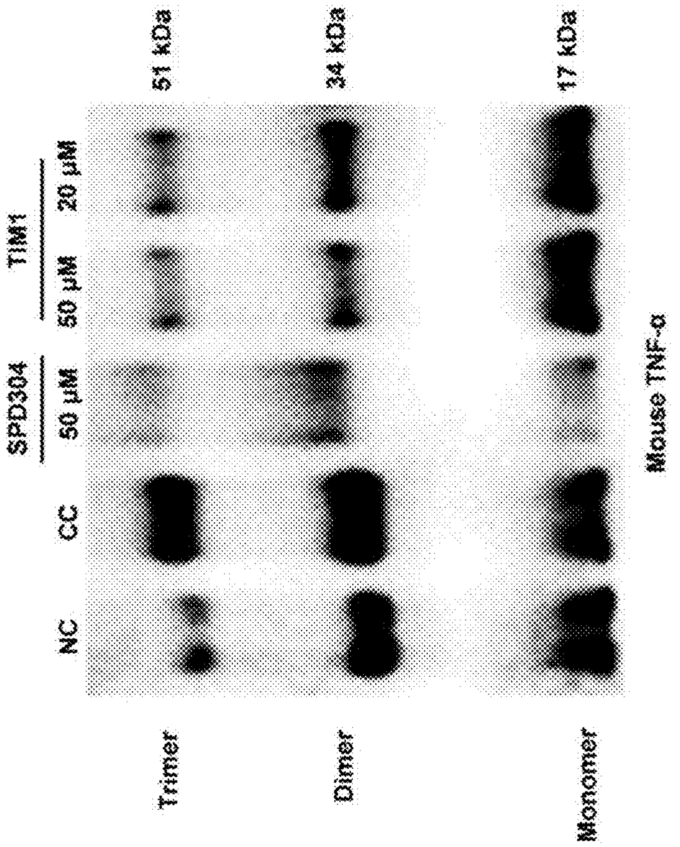
FIGS. 5A and 5B show the disruption of tumor necrosis factor α (TNF-α) homotrimerization by TIM1, in which, after TIM1 treatment, dissociation of the recombinant human TNF-α homotrimerization assembly (FIG. 5A) and dissociation of the recombinant mouse TNF-α homotrimerization assembly (FIG. 5B) are shown, in which human and mouse TNF-α were incubated with TIM1 or SPD304, chemically cross-linked, and then subjected to Western blotting, NC representing non-cross-linked control (no cross-linker, no inhibitor), CC representing cross-linked control (no inhibitor), and blotting being visualized with a CHEMIDOC™ Touch Imaging System (Bio-Rad Laboratories).
Figure 5A:
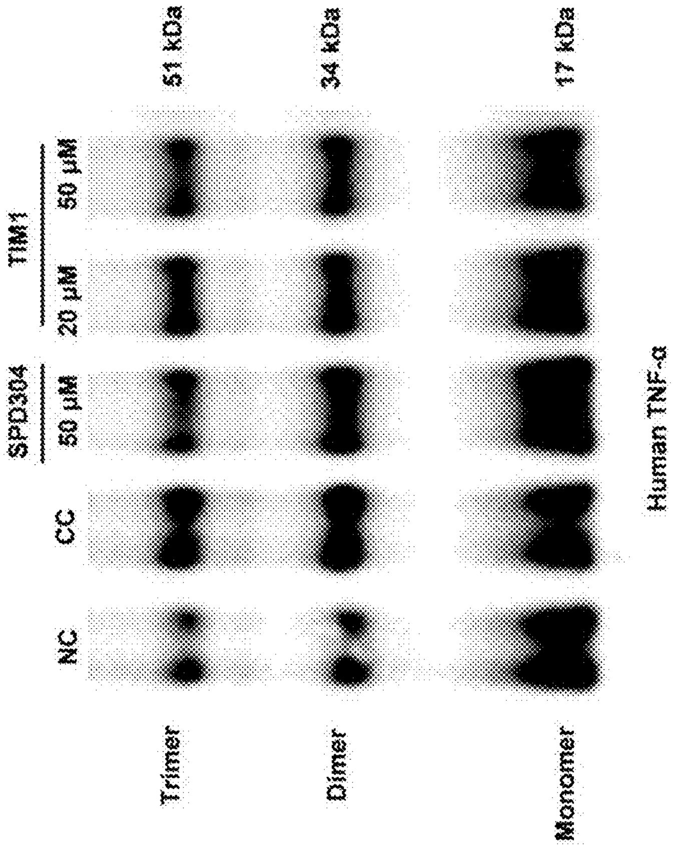

Example 5: Confirmation of Effect of TIM1 on Preventing TNF-α Homotrimerization Assembly After confirming the effect of TIM1 on inhibiting the TNF-α signaling pathway, the mechanism of action thereof was verified through cross-linked protein interaction analysis followed by Western blotting analysis. It is known that TNF-α is a stable homotrimer in a solution and is biologically active, and also that ligands interfering with trimeric assembly inactivate cytokine functions (Melagraki G. et al. (2017) *PLoS Comput. Biol.* 13(4):e1005372). Since the initial screening of ligands was performed in consideration of the small-molecule binding site of the TNF-α conformation, it was expected that TIM1 should block TNF-α activity by inhibiting the formation of a functional trimer. To this end, rhTNF-α was pre-cultured with TIM1 or SPD304, chemically cross-linked, and then analyzed through Western blotting. As expected, TIM1 inhibited the formation of functional homotrimers in both rhTNF-α and rmTNF-α in a concentration-dependent manner (FIGS. 5A and 5B). This indicates that TIM1 binds very specifically to the central hydrophobic cavity of the preformed TNF-α homodimer, thus preventing spatial binding of the third monomer under physiological conditions.

Figure 6A:
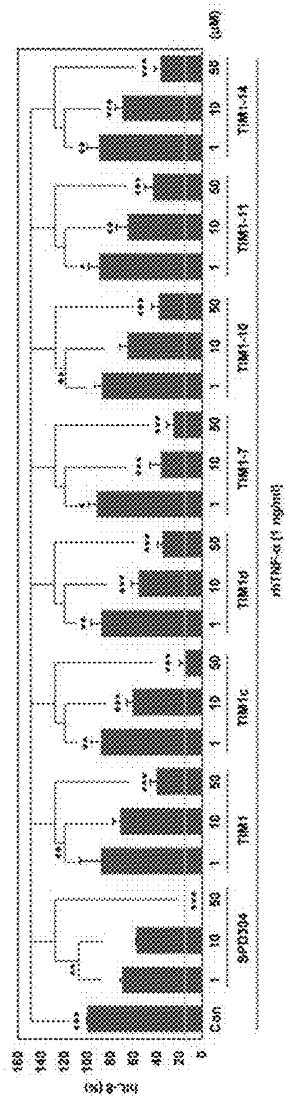
FIGS. 6A to 6F show a comparison of the in vitro activity of TIM1 derivatives and behavioral assessment of the anti-arthritic activity of TIM1c in a mouse model of collagen-induced polyarthritis.

Example 6: Confirmation of Improved Bioactivity of TIM1 Derivatives on TNF-α Signaling In order to improve the TNF-inhibitory activity of TIM1, further experiments were performed using a subset of commercially available (80% similar) derivatives, and the activity thereof was compared to TIM1 or SPD304. HDFs were cultured with pre-cultured mixtures of rhTNF-α with TIM1, TIM1-derivatives, or SPD304, and the culture supernatants were assessed for secretion levels of hIL-8 through ELISA. Among the molecules tested, TIM1c, TIM1d, TIM1-7, TIM1-10, TIM1-11, and TIM1-14 (FIG. 9) showed negligible cytotoxicity and exhibited concentration-dependent inhibition of TNF-induced hIL-8 greater than that of TIM1 (FIG. 6A). In particular, TIM1c maximally inhibited TNF-induced hIL-8 compared to the others, and was considered the most potent derivative. It should be noted herein that SPD304 completely inhibits cytokine production at 50 μM, but exhibits strong cytotoxicity at concentrations exceeding 1 μM, making the observed cytokine inhibition insignificant.

Figure 6B:
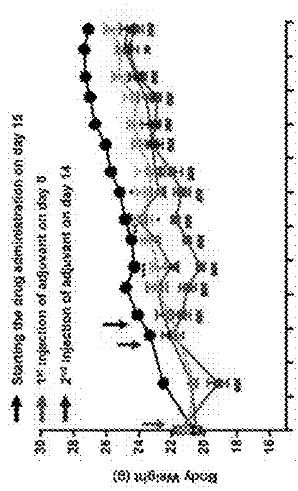
Figure 6C:
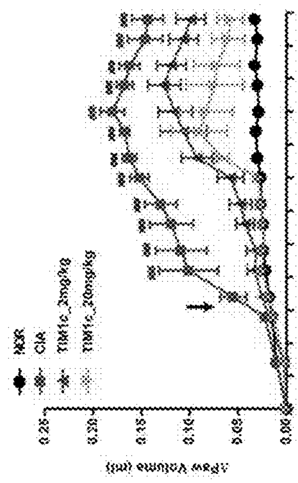
Figure 6D:
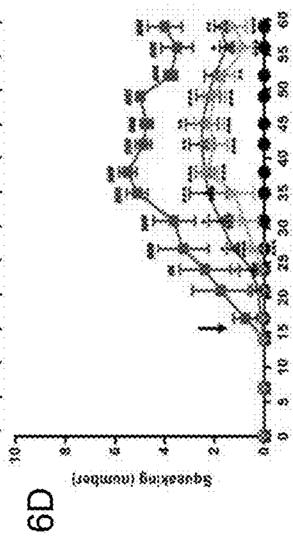
Figure 6E:
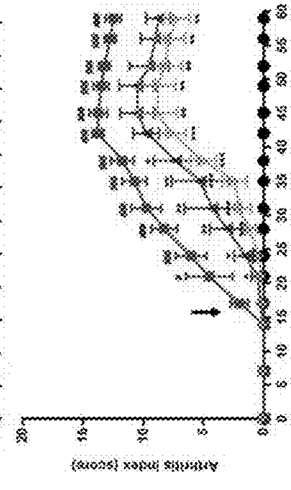
Figure 6F:
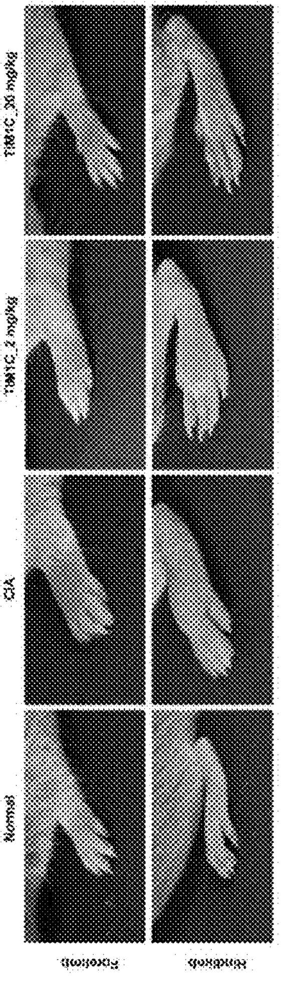

Example 7: Confirmation of Oral Bioavailability of TIM1c and Suppressed Arthritis Symptoms in Mice Due to strong TNF-α signaling inhibition of TIM1c in vitro, the present inventors predicted that rheumatoid arthritis (RA) symptoms could be ameliorated in animals. In a mouse model of collagen-induced polyarthritis (CIA), the efficacy of TIM1c was analyzed by feeding the animals with 2 or 20 mg/kg of the compound every 2 days (FIG. 10) and evaluating arthritis symptoms. Dose-dependent amelioration was exhibited in RA of the group treated through oral administration of TIM1c when compared to CIA mice, as confirmed by weight gain (FIG. 6B), paw volume decrease (FIG. 6C), and number of squeaks per day (FIG. 6D). Consequently, the arthritis index (clinical score) of the treatment group was significantly decreased compared to the case of CIA (FIG. 6E). At the start of drug treatment (day 15), the knees, ankles and paws were swollen, so the development of RA was evident in all forelimbs and hindlimbs (FIG. 6F). At a low dose of 2 mg/kg/2 days, TIM1c was able to slightly ameliorate disease severity. However, at a dose of 20 mg/kg/2 days, the induction of RA was significantly decreased to such an extent that the limbs of the animals were almost identical to those of the normal group. This suggests that oral administration of TIM1c exhibits an anti-inflammatory efficacy and effect in animals.

Figure 7A:
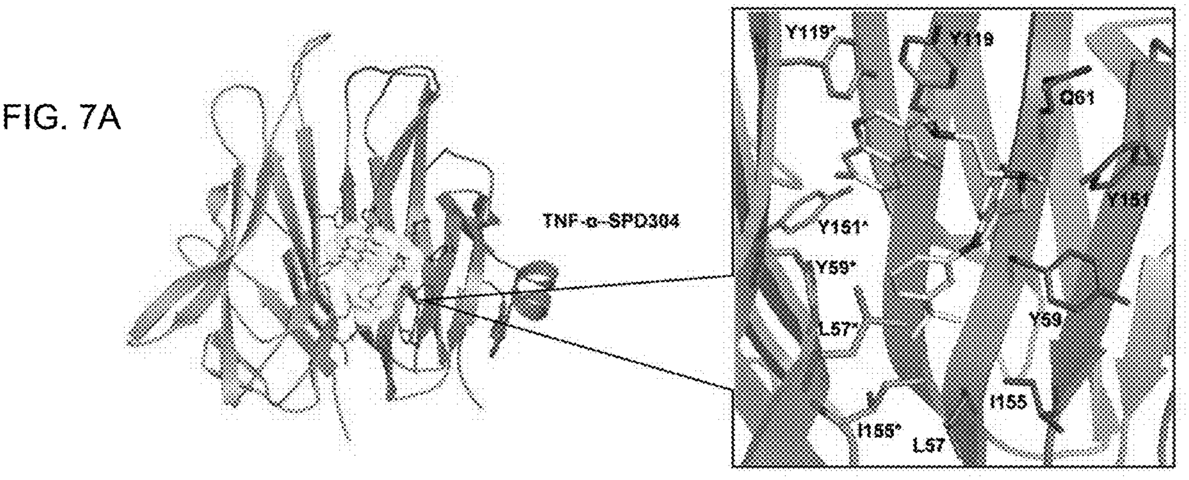
FIGS. 7A to 7C show the intermolecular interaction of TIM1, TIM1c, or SPD304 with TNF-α.
Figure 7B:
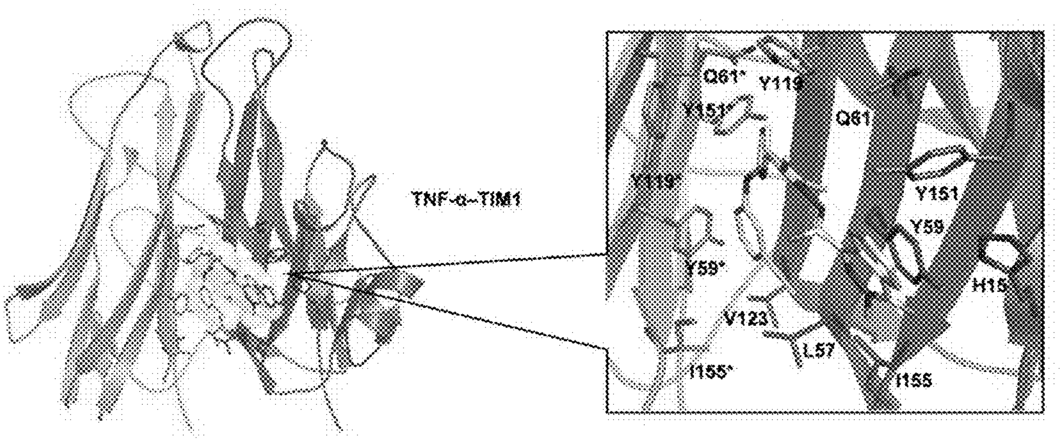
Figure 11:
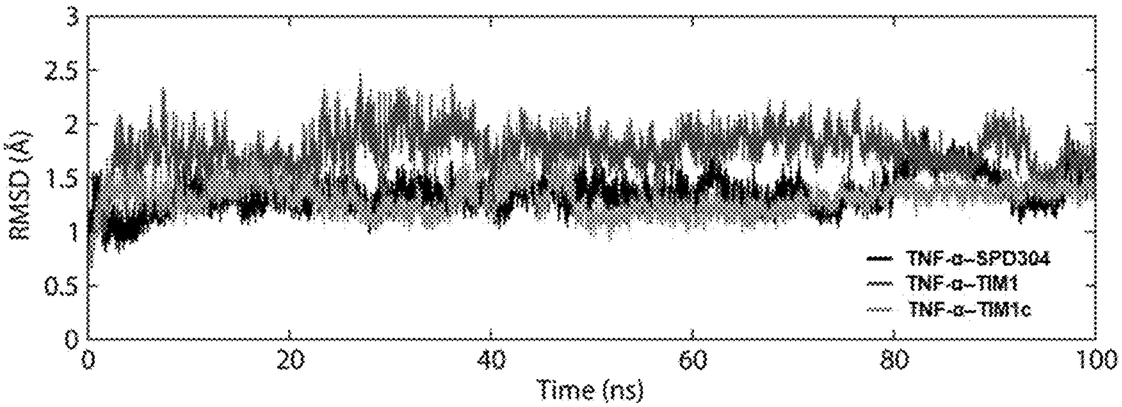
FIG. 11 shows the root-mean-square deviation (RMSD) of the distances between the backbone atoms of TNF-α-SPD304 (black), TNF-α-TIM1 (red), and TNF-α-TIM1c (green) as a function of 100 ns molecular mechanics simulation time.

Example 8: TIM1 and TIM1c Stably Occupying TNF-α Homodimer Through Non-Polar Interaction The present inventors performed molecular dynamics (MD) simulations of TNF-α-SPD304, TNF-α-TIM1, and TNF-α-TIM1c complexes for 100 ns in order to compare ligand-binding patterns under dynamic conditions (FIG. 11). The initial lead material TIM1 was bound to the TNF-α dimer in a more expanded form than SPD304 (FIG. 7A), and the thiazole ring was packed for Y119/Y119* represents chain B) and a carboxamide-linked pyrrole group that interacts mainly with Q61 and Y151 (FIG. 7B). The phthalazine group was stabilized through hydrophobic contact with Y151 and H15 as well as partial n-stacking interactions with Y59. The ethynylphenyl group interacted with V123, L57 and I155, and also interacted with Y151*, Y59* and I155*. With the exception of the electrostatic interaction alone between the amide-nitrogen of TIM1 and the hydroxyl group of the Y151 side chain, TIM1 did not form any salt bridge or hydrogen bond with TNF-α. The electronegative atom of SPD304 (e.g. 3-trifluoromethyl moiety) interacted with the core and was exposed toward the oxygen solvent of the ligand.

Figure 7C:
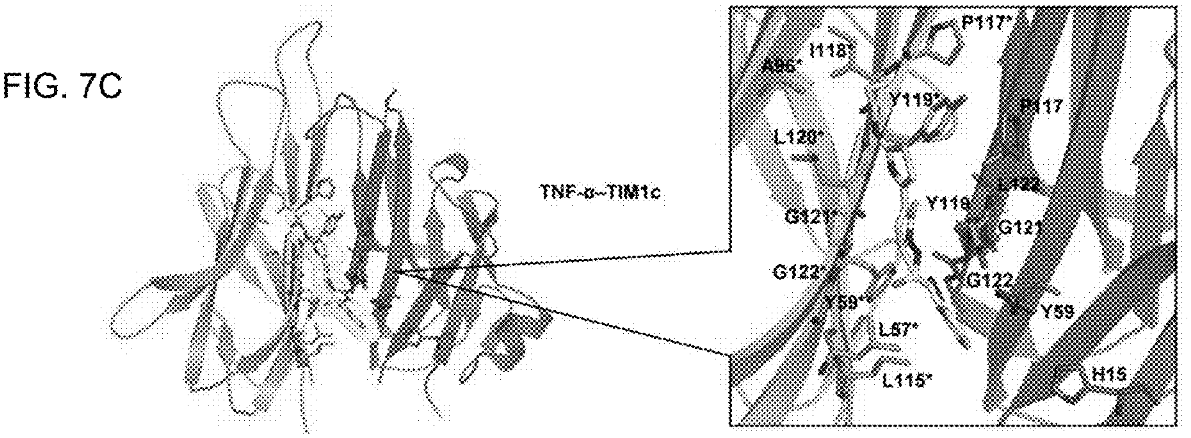

Also, TIM1c was bound to the TNF homodimer fully in an unfolding direction but partially in a planar direction (FIG. 7C). In TIM1c, the ethynylphenyl group is substituted with a propylamino group, which is extended toward the hydrophobic pocket formed by A96*, P117*, I118* and L120*. Unlike TIM1, the thiazole ring and carboxamide-linked pyrrole group of TIM1c were packed only for Y119/Y119*, which showed a distinct orientation compared to the other two complexes. The phthalazine group was stabilized through hydrophobic contact with Y59*, L57*, L115* and H15, as well as partial π-stacking interactions with Y119 and Y59. As in SPD304, the hydrophobic ring system of TIM1c came into close contact with β-strands (L120-G121-G122) of both subunits of TNF-α.

MM/PBSA binding affinity calculation showed that the total binding free energy values of TIM1 and TIM1c were less than that of SPD304, but the van der Waals (vdW) interaction energy values thereof were relatively larger (Table 4).

TABLE 4

Binding free energy (kJ $mol^{-1}$) decomposition of TNF-α-ligand complexes

| System | $^1\Delta_{vdW}$ | $^2\Delta_{elec}$ | $^3\Delta_{ps}$ | $^4\Delta_{SASA}$ | $^5\Delta G_{Total}$ |
|---|---|---|---|---|---|
| TNF-α/SPD304 | −152.82 ± 5.85 | −107.36 ± 6.32 | 98.6 ± 5.45 | −14.78 ± 5.0 | −176.37 ± 7.56 |
| TNF-α-TIM1c | −164.18 ± 4.8 | −22.64 ± 5.01 | 45.46 ± 9.12 | −14.36 ± 3.98 | −155.72 ± 3.65 |
| TNF-α/TIM1 | −203.39 ± 7.26 | −25.19 ± 5.74 | 92.72 ± 5.42 | −17.93 ± 1.2 | −153.78 ± 4.48 |
| TNF-α/JNJ525 | −178.29 ± 6.16 | −32.29 ± 5.54 | 89.62 ± 4.49 | −15.83 ± 2.2 | −136.79 ± 4.48 |

[1]Van der Waals energy, [2]Electrostatic energy, [3]Polar solvation energy, [4]Solvent-accessible surface area energy, [5]Total binding free energy.

The greater binding affinity between TNF-α and SPD304 results from the higher electrostatic interaction energy, which may be due to the 3-trifluoromethyl group of the ligand. TIM1c exhibited slightly higher binding affinity for TNF-α, possibly due to the low contribution to solvent-accessible surface area energy of the complex and polar solvation. Considering that the ligand-binding site in TNF-α is predominantly non-polar, it is likely that the ligand-receptor complex having larger intermolecular non-polar or vdW interaction energy has stronger binding force.

INDUSTRIAL APPLICABILITY

According to the present invention, novel small-molecule inhibitors of TNF-α were discovered using computer-aided virtual screening, and these inhibitors were experimentally verified through cell-based biopsy and in a mouse model of collagen-induced arthritis. Extracellular inactivation of TNF-α due to disruption of the protein-protein interface is the most innovative and effective method for alleviating a chronic systemic inflammatory status, and TIM series compounds, having effective efficacy, low toxicity, and oral bioavailability compared to existing TNF inhibitors, can be useful as anti-inflammatory lead molecules.

Although specific embodiments of the present invention have been disclosed in detail above, it will be obvious to those of ordinary skill in the art that the description is merely of preferable exemplary embodiments and is not to be construed as limiting the scope of the present invention. Therefore, the substantial scope of the present invention is to be defined by the appended claims and equivalents thereof.

The invention claimed is:

1. A method for inhibiting TNF-α in a subject in need thereof comprising administering a compound of Chemical Formula 1 below or a pharmaceutically acceptable salt thereof or a composition comprising the same to the subject:

[Chemical Formula 1]

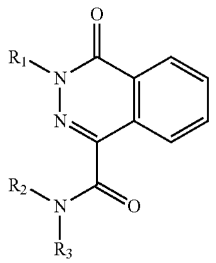

in Chemical Formula 1, $R_1$ to $R_3$ are each independently a hydrogen atom, straight or branched alkyl, amino, alkylamino, arylamino, hydroxy, halogen, nitrile group, nitro group, cycloalkyl, haloalkyl, allyl, alkoxy, alkylcarbonyl, cycloalkylcarbonyl, arylcarbonyl, alkylarylcarbonyl, alkoxycarbonyl, cycloalkoxy, substituted or unsubstituted aryl, heteroaryl, heterocycloalkyl, aryloxy, alkoxyheteroaryl, heteroaryloxyalkyl, alkylheteroaryl, alkylaryl, arylalkyl, alkylheteroaryl, alkylester, alkylamide, or acryl, wherein the alkyl, alkylamino, or alkoxy is $C_{1-30}$, the cycloalkyl is $C_{3-30}$, the allyl is $C_{2-30}$, the aryl is $C_{6-30}$, and the heteroaryl and heterocycloalkyl contain a heteroatom selected from among oxygen (O), sulfur(S), and nitrogen (N).

2. The method according to claim 1, wherein $R_1$, $R_2$, and $R_3$ are a substituent selected from the group consisting of:

$R_1$: $C_{1-6}$ alkyl; and $R_2$ and $R_3$: a hydrogen atom, aryl,

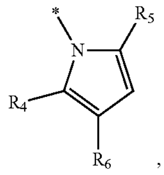 , 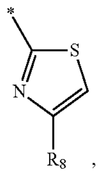 , or 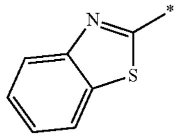

wherein $R_2$ and $R_3$ are same as or different from each other, $R_4$ and $R_5$ are same as or different from each other and are $C_{1-6}$ alkyl;

$R_6$ is

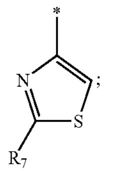

$R_7$ is $C_{1-6}$ alkylamino, or substituted or unsubstituted arylamino;

$R_8$ is $C_{1-6}$ alkyl or

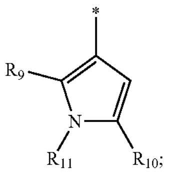

and $R_9$ to $R_{11}$ are $C_{1-6}$ alkyl or arylalkyl.

3. The method according to claim 2, wherein $R_1$, $R_2$, and $R_3$ are a substituent selected from the group consisting of:

$R_1$: $C_{1-6}$ alkyl; and $R_2$ and $R_3$: a hydrogen atom, aryl,

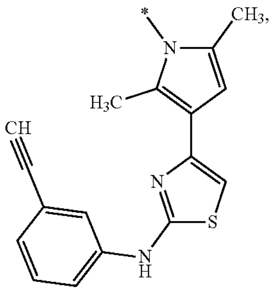

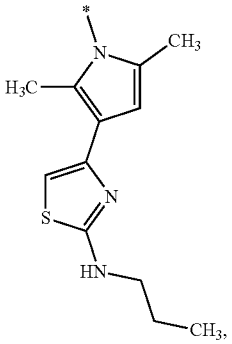

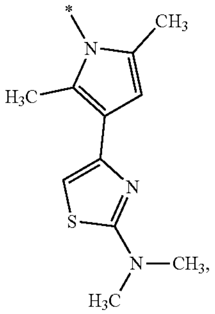

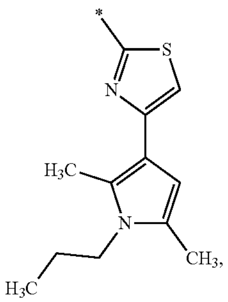

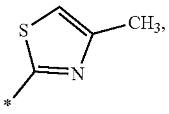

-continued
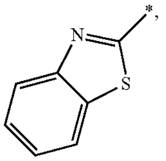
or
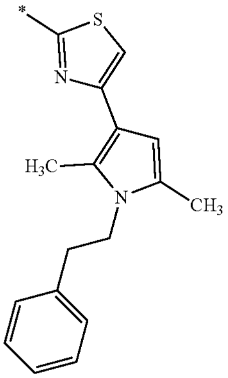
wherein $R_2$ and $R_3$ are same as or different from each other.
4. The method according to claim 1, wherein the compound of Chemical Formula 1 is any one compound selected from the group consisting of Chemical Formula 1-1 to Chemical Formula 1-7 below:
[Chemical Formula 1-1]
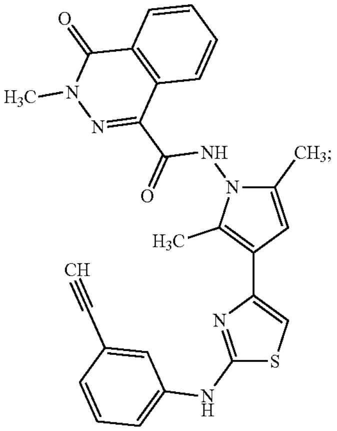
[Chemical Formula 1-2]
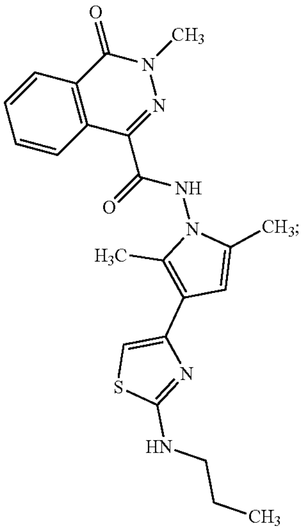
-continued
[Chemical Formula 1-3]
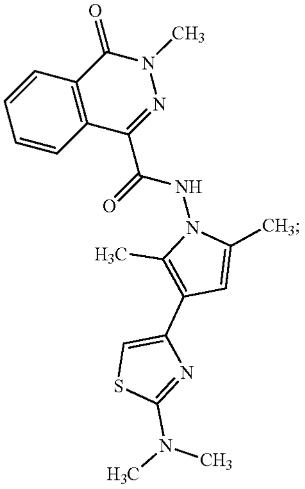
[Chemical Formula 1-4]
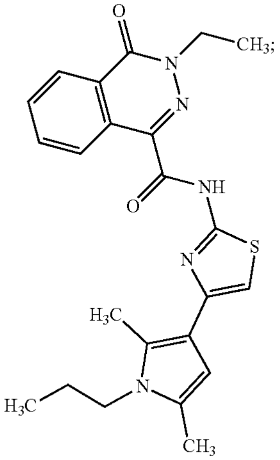
[Chemical Formula 1-5]
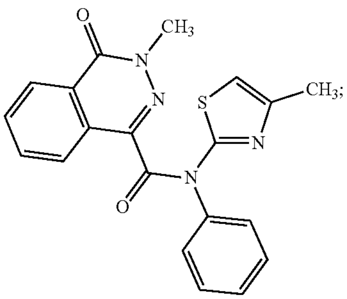

-continued
[Chemical Formula 1-6]
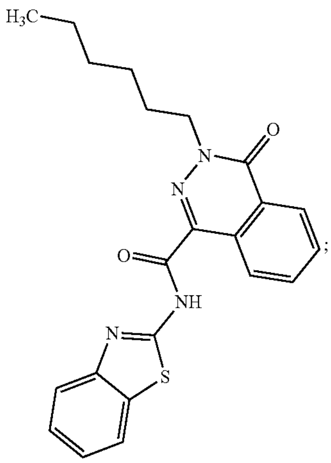
; and
-continued
[Chemical Formula 1-7]
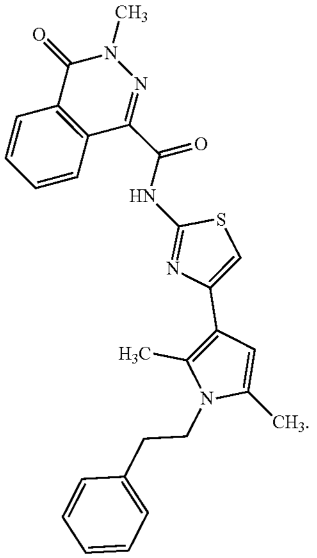
5. The method according to claim 1, wherein the compound inhibits formation of a TNF-α homotrimer by specifically binding to a binding cavity of a TNF-α homodimer.
* * * * *